(12) United States Patent
Gareau

(10) Patent No.: US 10,307,098 B2
(45) Date of Patent: Jun. 4, 2019

(54) SYSTEM AND METHOD FOR OPTICAL DETECTION OF SKIN DISEASE

(71) Applicant: The Rockefeller University, New York, NY (US)

(72) Inventor: Daniel Gareau, New York, NY (US)

(73) Assignee: THE ROCKEFELLER UNIVERSITY, New York, NY (US)

(*) Notice: Subject to any disclaimer, the term of this patent is extended or adjusted under 35 U.S.C. 154(b) by 0 days.

(21) Appl. No.: 14/907,208

(22) PCT Filed: Jul. 22, 2014

(86) PCT No.: PCT/US2014/047636
§ 371 (c)(1),
(2) Date: Jan. 22, 2016

(87) PCT Pub. No.: WO2015/013288
PCT Pub. Date: Jan. 29, 2015

(65) Prior Publication Data
US 2016/0166194 A1    Jun. 16, 2016

Related U.S. Application Data

(63) Continuation of application No. 14/051,053, filed on Oct. 10, 2013, now Pat. No. 10,182,757.
(Continued)

(51) Int. Cl.
| | |
|---|---|
| *A61B 5/00* | (2006.01) |
| *A61B 5/1455* | (2006.01) |
| *A61B 5/145* | (2006.01) |

(52) U.S. Cl.
CPC .......... *A61B 5/444* (2013.01); *A61B 5/0075* (2013.01); *A61B 5/14546* (2013.01);
(Continued)

(58) Field of Classification Search
None
See application file for complete search history.

(56) References Cited

U.S. PATENT DOCUMENTS

| | | |
|---|---|---|
| 5,016,173 A | 4/1991 | Kenet et al. |
| 5,706,821 A | 1/1998 | Matcher |

(Continued)

FOREIGN PATENT DOCUMENTS

| | | |
|---|---|---|
| CN | 101686819 | 3/2010 |
| GB | 2502672 | 12/2013 |

(Continued)

OTHER PUBLICATIONS

International Search Report issued for International Application No. PCT/US14/47636, dated Feb. 13, 2015.
(Continued)

*Primary Examiner* — Erica S Lee
(74) *Attorney, Agent, or Firm* — Pearl Cohen Zedek Latzer Baratz LLP

(57) ABSTRACT

An optical system for the detection of skin disease, such as melanoma, acquires images of a lesion on a subject's skin at different wavelengths and utilizes a sweeping arm rotating about the lesion in a clock-like sweep to produce diagnostically relevant metrics and classifiers from the image data so as to enhance detection of the skin disease.

20 Claims, 18 Drawing Sheets

Related U.S. Application Data

(60) Provisional application No. 61/857,143, filed on Jul. 22, 2013.

(52) U.S. Cl.
CPC ...... *A61B 5/14551* (2013.01); *A61B 5/14552* (2013.01); *A61B 5/443* (2013.01); *A61B 5/6898* (2013.01); *A61B 2560/0431* (2013.01); *A61B 2576/00* (2013.01)

(56) References Cited

U.S. PATENT DOCUMENTS

| | | | |
|---|---|---|---|
| 5,944,598 A | 8/1999 | Tong | |
| 6,208,749 B1 | 3/2001 | Gutkowics-Krusin et al. | |
| 7,006,223 B2 | 2/2006 | Mullani | |
| 7,027,153 B2 | 4/2006 | Mullani | |
| 7,167,243 B2 | 1/2007 | Mullani | |
| 7,167,244 B2 | 1/2007 | Mullani | |
| 7,603,031 B1 | 10/2009 | Vlaud | |
| 7,894,651 B2 | 2/2011 | Gutkowics-Krusin et al. | |
| 8,218,862 B2 | 7/2012 | Demirti | |
| 8,498,460 B2 | 7/2013 | Patwardhan | |
| 8,971,609 B2 | 3/2015 | Gareau et al. | |
| 10,182,757 B2* | 1/2019 | Gareau | A61B 5/6898 |
| 2003/0078482 A1* | 4/2003 | Kenan | A61B 5/0536 600/372 |
| 2004/0267102 A1 | 12/2004 | Skladnev | |
| 2005/0228264 A1* | 10/2005 | Grichnik | A61B 5/0059 600/411 |
| 2008/0123106 A1 | 5/2008 | Zeng et al. | |
| 2008/0132794 A1 | 6/2008 | Alfano et al. | |
| 2008/0214907 A1 | 9/2008 | Gutkowicz-Krusin et al. | |
| 2008/0275315 A1 | 11/2008 | Oka et al. | |
| 2009/0016491 A1 | 1/2009 | Li | |
| 2009/0220415 A1 | 9/2009 | Shachaf et al. | |
| 2009/0279760 A1 | 11/2009 | Bergman | |
| 2010/0185064 A1 | 7/2010 | Bandic | |
| 2010/0255795 A1 | 10/2010 | Rubinsky et al. | |
| 2010/0271470 A1 | 10/2010 | Stephan et al. | |
| 2010/0302358 A1* | 12/2010 | Chen | A61B 5/0059 348/77 |
| 2011/0013006 A1 | 1/2011 | Uzenbajakava et al. | |
| 2012/0041285 A1 | 2/2012 | Krishnan et al. | |
| 2012/0170828 A1 | 7/2012 | Gareau et al. | |
| 2012/0172685 A1 | 7/2012 | Gilbert | |
| 2012/0259229 A1* | 10/2012 | Wang | A61B 5/0075 600/476 |
| 2012/0320340 A1 | 12/2012 | Coleman, III | |
| 2013/0014868 A1 | 1/2013 | Ishida | |
| 2013/0053701 A1 | 2/2013 | Weist et al. | |
| 2013/0108981 A1* | 5/2013 | Duret | A61B 1/24 433/30 |
| 2014/0036054 A1* | 2/2014 | Zouridakis | G06T 7/0012 348/77 |
| 2014/0213909 A1* | 7/2014 | Mestha | A61B 5/0077 600/476 |
| 2015/0025343 A1 | 1/2015 | Gareau et al. | |
| 2015/0082498 A1* | 3/2015 | Meyer | G01Q 30/02 850/1 |

FOREIGN PATENT DOCUMENTS

| | | |
|---|---|---|
| JP | 2005192944 | 5/2005 |
| WO | WO 90/13901 | 11/1990 |
| WO | WO 2011/087807 | 7/2011 |
| WO | WO2012/162596 | 11/2012 |
| WO | WO2015/013288 | 1/2015 |

OTHER PUBLICATIONS

"Melanoma." Skin Cancer. Skin Cancer Foundation n. d. Web. Jul. 29, 2013. <http://www.skincancer.org/skin-cancer-information/melanoma>.

Busam, Klaus J., Ashfaq A. Marghoob and Allan Halpern. "Melanoma Diagnosis by Confocal Microscopy: Promise and Pitfalls." Journal of Investigative Dermatology. 125.3 (2005): n. page. Print.

Gareau, Daniel S., Glenn Merlino, Christopher Corless, Molly Kulesz-Martin, and Steven L. Jacques. "Noninvasive Imaging of Metanoma with Reflectance Mode Confocal Scanning Laser Microscopy in a Murine Model." Journal of Investigative Dermatology. (2007): n. page. Print.

Gareau, Dan "Automated identification of epidermal keratinocytes in reflectance confocal microscopy". Journal of Biomedical Optics. 16.3 (2011): n. page. Print.

Gareau, Dan, Ricky Hennessy, Eric Wan, Giovanni Pellacani and Steven L. Jacques. "Automated detection of malignant features in confocal microscopy on superficial spreading melanoma versus nevi." Journal of Biomedical Optics.15.6(2010): n. page. Print.

Nehal, Kilshwer S., Dan Gareau, and Milind Rajadhyaksha. "Skin Imaging With Reflectance Confocal Microscopy." Seminars in Cutaneous Medicine and Surgery. 27. (2008): 37-43. Print.

Office Action dated Jun. 20, 2017 in U.S. Appl. No. 14/051,053.

European Search Report dated Mar. 2, 2017 for Application 14829442. 4.

International Preliminary Report on Patentability for PCT application No. PCT/US2016/047065 dated Feb. 22, 2018.

Office Action for Chinese patent application No. CN201480052009. 5.

Argenziano, G. et al., Dermoscopy improves accuracy of primary care physicians to triage lesions suggestive of skin cancer. J Clin Oncol, 2006. 24(12): p. 1877-82.

Artificial intelligence—how far can it go in dermatology? Modernizing Medicine Jul. 12, 2016; Available from: https://www.modmed.com/artificial-intelligence-how-far-can-it-go-in-dermatology/.

Breiman, L., Random Forests. Machine Learning, 45, 2001 Kluwer Academic Publishers 5-32.

Cortes, C. and V. Vapnik, Support-vector networks. Machine Learning, 1995. 20(3): p. 273-297.

Doyle-Lindrud, S., Watson will see you now: a supercomputer to help clinicians make informed treatment decisions. Clin J Oncol Nurs, 2015.19(1): p. 31-2.

Drugge, R.J., et al., Melanoma screening with serial whole body photographic change detection using Melanoscan technology, Dermatol Online J, 2009. 15(6): p. 1.

Elder, D.E., Dysplastic naevi: an update. Histopathology, 2010, 56(1): p. 112-20.

Emery, J.D., et al., Accuracy of SIAscopy for pigmented skin lesions encountered in primary care: development and validation of a new diagnostic algorithm. BMC Dermatol, 2010. 10: p. 9.

Fisher, R.A., The use of multiple measurements in taxonomic problems. Annals of Eugenics, 1936.7: p. 179-188.

Fix, E. and J.L. Hodges, Discriminatory Analysis, nonparametric discrimination: Consistency properties. 1951.

Friedman, J.H., Multivariate Adaptive Regression Splines. The Annals of Statistics, 1991, 19(1): p. 1-67.

Friedman, J., T. Hastie, and R. Tibshirani, Regularization Paths for Generalized Linear Models via Coordinate Descent. Journal of Statistical Software, 2010. 33(1): 1-22.

Friedman, Robert J., et al., The Diagnostic Performance of Expert Dermoscopists vs a Computer-Vision System on Small-Diameter Melanomas, Arch Dermatol. 2008;144(4):476-482.

Henning, J. Scott, et al., The CASH (color, architecture, symmetry, and homogeneity) algorithm for dermoscopy, J Am Acad Dermatol 2007;56:45-52.

Hofner, B., et al., Model-based boosting in R: a hands-on tutorial using the R package mboost. Computational Statistics, 2012, 29(1-2): p. 3-35.

IBM detects skin cancer more quickly with visual machine learning. Computer World News; Available from: http://www. computerworld.com/article/2860758/ibm-detects-skin-cancer-more-quickly-with-visual-machine-learning.html.

Malvehy, J., et al., Clinical performance of the Nevisense system in cutaneous melanoma detection: an international, multicentre, prospective and blinded clinical trial on efficacy and safety. Br J Dermatol, 2014. 171 (5): p. 1099-107.

(56) References Cited

OTHER PUBLICATIONS

Memorial Sloan Kettering Trains IBM Watson to Help Doctors Make Better Cancer Treatment Choice 2014; Available from: https://www.mskec.org/blog/msk-trains-ibm-watson-help-doctors-make-better-treatment-choices.
Menzies, S.W., et al., The performance of SolarScan: an automated dermoscopy image analysis instrument for the diagnosis of primary melanoma. Arch Dermatol, 2005. 141 (11): p. 1388-96.
Monheit. G., et al., The performance of MelaFind: a prospective multicenter study. Arch Dermatol, 2011. 147(2): p. 188-94.
Nachbar, F., et al., The ABCD rule of dermatoscopy. High prospective value in the diagnosis of doubtful melanocytic skin lesions. J Am Acad Dermatol, 1994.30(4): p. 551-9.
Otsu, N., A threshold selection method from gray-level histogram. IEEE Transactions on System Man Cybernetics., 1979. SMC-9(1): p. 62-66.
Ramezani, M., et al., Automatic Detection of Malignant Melanoma using Macroscopic Images. J Med Signals Sens, 2014.4(4): p. 281-90.
Rigel, D.S., et al.. The evolution of melanoma diagnosis: 25 years beyond the ABCDs. CA Cancer J Olin, 2010. 60 (5): p. 301-16.
Rokach, L. Ensemble-based classifiers. Artificial Intelligence Review, 2010. 33: p. 1-39.
Rosipal, R. et al., Overview and Recent Advances in Partial Least Squares, in Subspace, Latent Structure and Feature Selection, C. Saunders, et al., Editors. 2006, Springer Berlin Heidelberg. p. 34-51.
Sgouros, D., et al., Assessment of SIAscopy in the triage of suspicious skin tumours. Skin Res Technol, 2014; 0:1-5.
Vestergaard, M.E., et al., Dermoscopy compared with naked eye examination for the diagnosis of primary melanoma: a meta-analysis of studies performed in a clinical setting, British Journal of Dermatology 2008 159, pp. 669-676.
Wolf, J A et al., Diagnostic inaccuracy of smartphone applications for melanoma detection-reply. JAMA Dermatol, 2013.149(4): p. 422-426.
Office Action for Japanese patent application No. 2016-529829 dated May 22, 2018.

\* cited by examiner

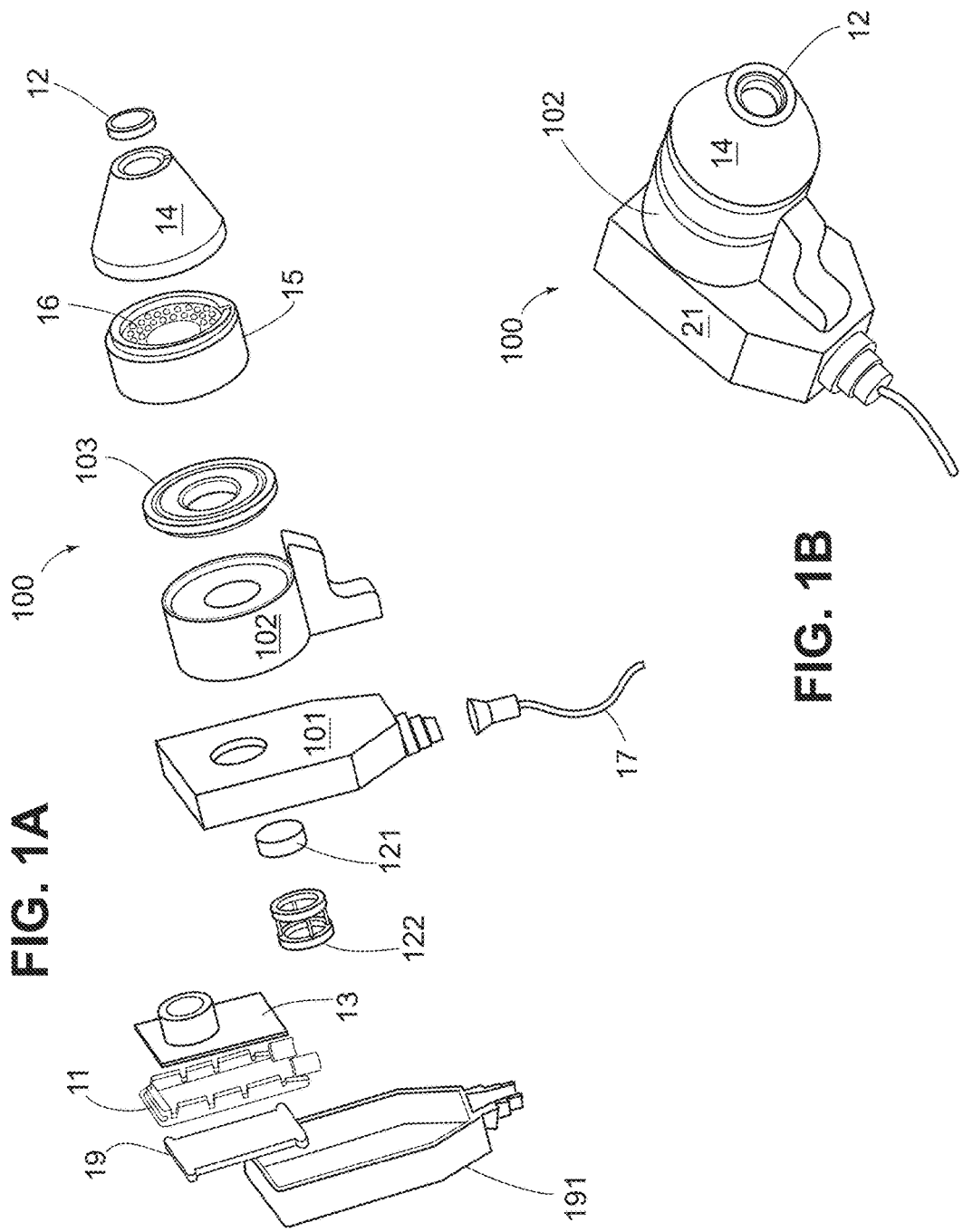

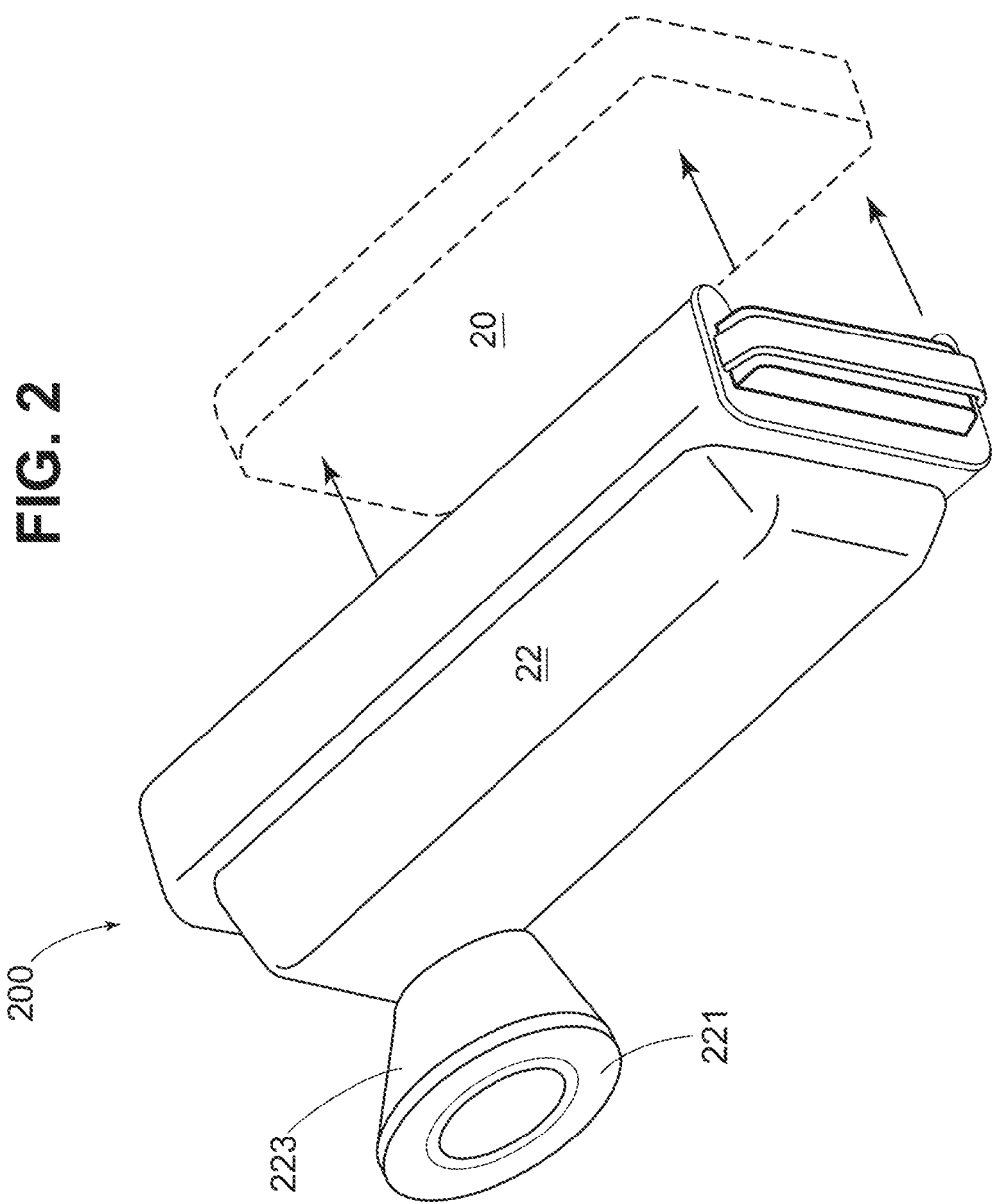

SYSTEM AND METHOD FOR OPTICAL DETECTION OF SKIN DISEASE

CROSS-REFERENCE TO RELATED APPLICATIONS

This application is a United States national stage application of International Application No. PCT/US14/47636, international filing date Jul. 22, 2014, which claims the benefit of U.S. application Ser. No. 14/051,053, filed Oct. 10, 2013 and U.S. Provisional Application No. 61/857,143, filed Jul. 22, 2013, all of which are incorporated by reference. A computer program listing submitted on CD-ROM is provided as a computer program listing appendix and is incorporated by reference. One disc is provided, with one file having file name Table 4. The listing describes and enables in detail the data processing steps described herein.

BACKGROUND OF THE INVENTION

Field of the Invention

The invention is directed to systems and methods for optical detection of skin disease and in particular apparatus and methods adapted to detect the presence of melanoma and to distinguish, for example, malignant melanoma from non-malignant dysplastic nevi and/or common nevi, using metrics and classifiers obtained from rotational analysis of image data obtained from a subject's skin lesion. The data obtained may be processed by one or more computer processors, and the processed data, a diagnosis or an indicator of the presence of absence of skin disease may be output to and displayed by one or more display modules.

Description of the Related Art

Melanoma, the most lethal skin cancer, incurs immense human and financial cost. Early detection is critical to prevent metastasis by removal of primary tumors. The early lateral growth phase is a vastly preferable detection window to the subsequent phase of metastatic initiation. Optical detection technologies for automated quantitative metrics of malignancy are needed to more accurately guide decisions regarding the need to biopsy and to make preoperative determination of adequate margins for surgical excision. After invasive biopsy or excision, diagnosis obtained by histopathologic evaluation is nearly 100% accurate; however deciding which lesions to biopsy is challenging. Only 3% to 25% of surgically-excised pigmented lesions are diagnosed as melanomas. Hence there is a need for noninvasive screening mechanisms that are both widespread and more accurate.

Dermoscopy is a common dermatological technique to evaluate skin lesions which may or may not be pigmented lesions. A dermatoscope typically consists of a light emitting diode (LED) illuminator, a low magnification microscope, and a clear window surface to flatten the skin against. The use of polarization enables partial rejection of deeply penetrating light, which can enhance superficial features of particular diagnostic interest. A digital imaging camera may also be attached to the dermatoscope.

U.S. Pat. Nos. 7,006,223, 7,027,153, 7,167,243, and 7,167,244 describe handheld dermoscopic epiluminescence devices.

Methods and apparatuses for evaluating optical image data obtained from a skin lesion on a subject's body are taught in U.S. Pat. Nos. 6,208,749 and 7,894,651, assigned to Mela Sciences, Inc.

U.S. Pat. No. 7,603,031 is directed to a multi-flash wide-field photography system adapted for medical or cosmetic facial photography. U.S. Pat. No. 8,218,862 describes feature detection for computer aided skin analysis using related wide-field photographic techniques. U.S. Pat. No. 8,498,460 describes wide-field imaging methods and apparatuses used to estimate the diffuse reflection component of an image of tissue, such as skin, which can then be further processed to obtain red and brown pigmentation images to indicate the distribution of hemoglobin and melanin in the skin.

SUMMARY OF THE INVENTION

One of the objects of the present invention is to employ algorithms that perform evaluations of image data obtained from reflecting light off of skin lesions with greater sensitivity, specificity and overall diagnostic accuracy, and which can be used to produce diagnostically relevant quantitative metrics in real time, in some cases without further evaluation of the lesion. (It will be understood that this application sometimes refers to the image of the lesion and the lesion itself interchangeably.)

Another object of the invention is to combine a dermatoscope, digital camera and automated screening by computer vision to bridge the diagnostic accuracy gap between invasive and noninvasive pathological analyses. Though the sophistication of the human brain may never be matched by computers, the present invention provides at least three benefits over traditional dermatologist screening: standardization, quantification and the enhanced ability to perform brute-force calculations. As outlined in the following description and claims, objective analytical diagnostic technologies have the potential to dramatically improve the diagnostic accuracy of widespread melanoma screening.

In particular, using rotational analysis of image data obtained from a skin lesion yields improved diagnostic accuracy compared to the prior art. The novel mathematical descriptors generated by the polar transformation of the image data may be trained on a set of skin lesions of known pathology to yield classifiers which provide a percent likelihood that a given lesion is malignant melanoma, paired with a percentage uncertainty for the prediction. The invention also provides enhanced opportunities to visualize the data obtained. In addition to a standard red-green-blue (RGB) image of the lesion, the present invention provides the user (doctor or patient) with a version of the image with suspicious regions highlighted, and the user may toggle between these display modes. The user may cycle through a set of gray scale images obtained at different wavelengths. The display may be toggled between x-y coordinates and a brightness map in polar coordinates $(r, \theta)$. In addition, rotational analysis may be performed using a clock sweep arm integrated with imaging at successively finer resolution, such as confocal microscopy and Raman spectroscopy.

Still another object of the invention is to use a wide field imaging system to image a large portion of skin and identify one or more skin lesions for further analysis, and then use a second imaging system with a narrower field of view to conduct such analysis.

In one aspect, the invention is an apparatus for detecting skin disease in a lesion on a subject's skin, comprising: a mechanical fixture having a flat surface to position or press against the subject's skin to define a distal imaging plane containing said lesion; a camera adapted to obtain image data from the lesion; a processor adapted to process the image data with a clock-like sweep algorithm to obtain metrics and/or one or more classifiers defining the rotational symmetry of the pigmented lesion; and an output device that indicates a likelihood of the presence or absence of skin disease in the subject obtained from the metrics and/or one or more classifiers. In this context, "metrics and/or one or more classifiers" means the likelihood may be obtained from metrics, from one or more classifiers or from a combination of metrics and one or more classifiers.

The clock-like sweep algorithm, for example, evaluates the brightness of pixels on a line segment between the center of the lesion image and the lesion image border as the line segment rotates around the center of the lesion with one end of the line segment fixed at the center of the lesion image. Rotational symmetry refers to different information obtained on the line segment at different angular positions. Such information may be directly related to the image, such as the image brightness, or may be information indirectly related to the image such as the average pigmented network branch length for the pigmented network branches encountered by a line segment. In the case of indirect information, preprocessing of the image is completed to define such information for each part of the image. Continuing the example, a circle with uniform brightness throughout exhibits perfect rotational symmetry. However, if the distance from the border of the lesion to the center of the lesion is different at different angular positions, or if the brightness of pixels differs at different positions on the line segment, or at different angular positions of the line segment, then the lesion is not rotationally symmetric, but asymmetric. This asymmetry may be quantified and used to produce diagnostically relevant metrics and/or one or more classifiers.

In another aspect of the invention, the camera is adapted to obtain multispectral images. For example, the skin lesion is illuminated with an array of LEDs that emit light of different spectral profiles (including, importantly, one or more LEDs that emit light in the non-visible UV range, such as 300 nm to 400 nm). The camera acquires M images, storing each pixel in the image as a set of M numbers that form a spectral measurement, which are then fitted as the weighted sum of N chromophores.

In another aspect, the invention is a method for obtaining an indication of a likelihood of the presence or absence of skin disease in a lesion on a subject's skin, comprising the steps of illuminating the subject's skin including the lesion (preferably flattened); obtaining image data from the reflection of light off the illuminated subject's skin with a camera; and processing the image data with a computer processor adapted to implement a clock-like sweep algorithm to obtain diagnostically relevant metrics and/or one or more classifiers defining the rotational symmetry of the lesion on the subject's skin. In the method, at least one processor transforms the image data into diagnostically relevant metrics and/or one or more classifiers defining the rotational distribution of one or more properties selected from the group consisting of [a] spatial texture features; [b] brightness features; [c] features of the edge/border; [d] color variation; [e] variations in features of a pigmented network including the length, shape brightness and organization of pigmented network segments in the network; and [f] oxygen saturation of tissue as defined by the amount and ratio of oxyhemoglobin and deoxyhemoglobin. This group of properties may also include [g] the heterogeneity of pigment species such as eumelanin, pheomelanin and other species of pigment.

In still another aspect, the invention is embodied as a system for detecting skin disease in a skin lesion on a subject's skin utilizing a commercially-widespread imaging device, such as a cellular phone having an integrated processor and camera. In this embodiment, the image data may be obtained using an illumination system selected from an external illumination system or a built-in flash. As used herein, "cellular phone" includes, for example, a smart phone which has image capture capability, and may also have a built-in flash (which may or may not be disabled during image acquisition), image processing capability, the ability to download data processing applications, and/or transmit images for remote processing. The cellular phone processor is adapted (for example, by using an application downloaded to the cellular phone) to process image data obtained using a sweeping arm positioned between the border of the lesion and the center of the lesion and rotated with a clock-like sweep around the lesion to obtain metrics and/or one or more classifiers defining the rotational symmetry of the lesion and generate a display depicting regions of interest in the subject's skin and/or an indication of a likelihood of the presence or absence of skin disease in the subject.

Processed data obtained with a cellular phone application in the form of a diagnostic indication or a representation of a region of interest on the subject's skin may be transmitted to a remote processor. For example, a patient may photograph his or her lesion and transmit the image to a doctor's office, database or other facility for further processing. As used herein, "a display depicting regions of interest in the subject's skin and/or an indication of a likelihood of the presence or absence of skin disease in the subject" may mean that a display i) provides only a processed image of the lesion with regions highlighted, or ii) only an indication that skin disease is more or less likely to be present (for example in the form of a number or text), or iii) the display may provide both a processed image and an indication that skin disease is more or less likely to be present (which display formats may toggle back and forth). Other forms of display are also within the scope of this invention.

In yet still another aspect, the invention is a method of diagnostically imaging of one or more skin lesions on a subject's skin, comprising the steps of: illuminating with a first illumination system a first area on a subject's skin; obtaining wide field image data from the illuminated skin using a camera having a wide field of view; processing the wide field image data to identify a target area within the first area which includes at least one skin lesion; illuminating the target area with a second illumination system, and obtaining narrow field image data from the illuminated target area with a camera having a narrow field of view; and processing the narrow field image data to obtain diagnostic information pertaining to the at least one skin lesion.

These and other aspects of the invention are shown and described below.

BRIEF DESCRIPTION OF THE DRAWINGS

FIG. 1A is an exploded view of a clinical apparatus according to one embodiment of the invention.

FIG. 1B depicts the assembled apparatus of FIG. 1A.

FIG. 2 depicts a cellular phone having an integrated processor and camera and an attached fixture for mounting the camera against a subject's skin according to another embodiment of the invention.

DETAILED DESCRIPTION OF THE INVENTION

System and Apparatus

Figure 3A:
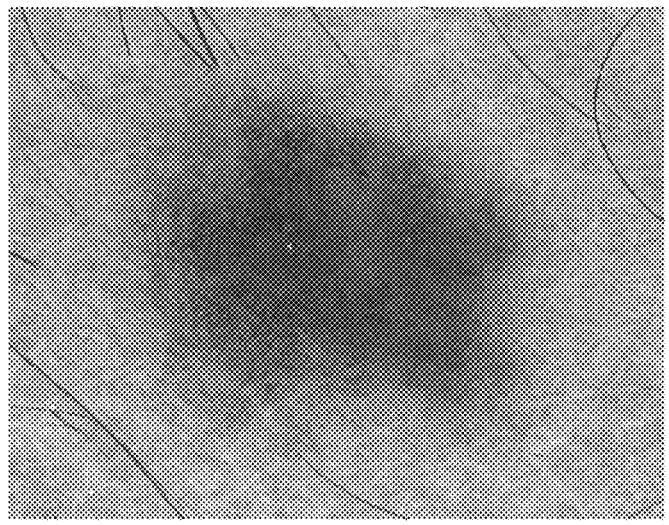
FIG. 3A and FIG. 3B depict the polar transformation of image data for a nevus.

One embodiment of the present invention is directed to a system including a camera, a mechanical fixture for illuminating the subject's skin and positioning the camera fixedly against the subject's skin, at least one processor adapted to perform the clock sweep algorithm, and at least one output device.

The camera is preferably a digital camera and may include a charged coupled device (CCD) sensor or complementary metal oxide semiconductor (CMOS), as known in the art. The camera may be a commercially available portable camera with an integrated illumination system or flash and a sensor array detecting Red Green and Blue (RGB) light. Alternatively an external illumination system may be provided and the camera sensor array may be adapted to receive "hyperspectral" light, meaning light divided into more spectral wavelength bands than the conventional RGB bands, which may be in both the visible and non-visible range. Hyperspectral imaging is described in more detail below.

In the clinical embodiment depicted in FIG. 1A, the camera is a circuit board level charge coupled device (CCD) detector imaging array mounted on a fixture that can be positioned or pressed against the subject's skin. In this embodiment, the mechanical fixture 100 includes a flat transparent plate 12 of glass, polycarbonate, polymethylmethacrylate (PMMA), UV-fused silica or the like, that may be positioned or pressed against the subject's skin so that the lesion stays in one plane (the distal imaging plane) when the image is obtained. Plate 12 may be mounted on a spacer, such as nose cone 14, which protects the camera lens aperture and provides an optimal distance between the illuminating and imaging apparatus and the lesion.

An illumination apparatus, such as LED mounting ring 15, includes LEDs positioned around the optical axis of the camera which may be located proximally of the distal imaging plane which frames the skin lesion, but still forward of the imaging apparatus. The illumination apparatus includes a set of devices that emit light of different spectral profiles to illuminate the skin lesion with light at desired wavelengths. In FIG. 1A, the LED mounting apparatus comprises a ring of light emitting diodes (LEDs) 16 each capable of emitting light at a specified wavelength in a range of 300 nm to 950 nm, preferably including at least one LED in the range of 300 to 400 nm, while the camera sequentially acquires images at the specified wavelengths. The apparatus may utilize commercially available LEDs which are inexpensive and widely available with various spectral characteristics. However, if more accurate and narrow spectra are desired, laser illumination elements or filters placed in front to sharpen the LED emission spectra may also be used.

The LED wavelengths are selected based on the methods used to extract relevant information from the image data to identify diagnostically relevant patterns in the lesion. For example, it is known in the art that blue light is absorbed by melanin (one of N chromophores in the skin). Thus, at least one of the LEDs in the array, and preferably a plurality, emit light in the violet-indigo-blue wavelength ranges, 400-500 nm Blood absorbs in the green, so that at least one of the LEDs in the array and preferably a plurality, emit light in the 500-600 nm wavelength range. Pigment at the deepest portion of a lesion, in a relatively deep lesion, has absorption shifted to the red, so that one or more LEDs emit light in the range of 600 nm to 750 nm, and even into the infrared (IR) (780 nm and above) which may be helpful to determine the deepest portion of a lesion to be excised, for example. Illumination in the non-visible ultraviolet (UV) range to obtain information about the skin lesion is another novel aspect of the invention. Thus at least one, and preferably a plurality of LEDs in the array, are adapted to illuminate the skin at a wavelength of 300 nm to 400 nm. At least one, and preferably a plurality of LEDs are adapted to illuminate the skin in accordance with the absorption profile of eu-melanin as distinct from the absorption profile of pheo-melanin. In this way, at each angular position of the sweeping arm, as the camera acquires M images at different wavelengths, each pixel in the image is stored as a set of M numbers that form a spectral measurement which may be fit as the weighted sum of N chromophores in the skin lesion.

In embodiments, particularly where off-the-shelf LEDs are used, the illumination system may comprise a set of LEDs having illumination spectra that overlap. In this case, correction may be made digitally, providing a processor adapted to remove overlapping regions of the spectra, thereby improving spectral resolution. For example, a set of LEDs may have spectra $L_1, L_2, L_3 \ldots L_n$ that overlap, and image data obtained at one illumination, $I\_L_i$, may be used to correct the illumination at $I\_(L_{i-1})$ by subtracting $C^*(I\_L_i)$ from $I\_(L_{i-1})$, where C is a constant related to the amount of overlap between the two spectra. Alternatively, during the fitting process wherein N chromophores are specified by fitting M reflectance values at the M wavelengths, the known absorption spectra of the chromophores can be integrated over each of the M LED emission spectra so that the absorption from each chromophore at each wavelength is uniquely specified.

The correction for overlapping spectra may be programmed in advance based on the specifications from the manufacturer of the LED. Alternatively, an apparatus according to the invention may be provided with an internal spectrometer to measure the emission spectra of the LED or other illumination device during the skin imaging or during calibration procedures, and that measurement may be used to implement the correction for overlapping spectra. A fiber optic element located distally of the illumination devices guides the actual emission spectra of each illumination device to the onboard spectrometer which provides the spectrum to the processor to perform the steps described above for resolving the overlapping spectra.

Thus, an appropriate array of LEDs for an illumination system may be selected from commercially available LEDs by the person of ordinary skill in the art, taking care to match the input requirements and output levels for different LEDs, as well as differences between output wavelengths provided in the manufacturer's specifications and measured wavelength. Preferably 3 to 50, and more preferably 10 to 30 LEDs are included in an array.

Conventional dermoscopy, with imaging by the eye or by conventional digital cameras, illuminated with white light and obtained three intensity images at the red, green and blue (RGB) wavelength ranges where the three cones in the human retina are sensitive. RGB imaging technology in a conventional digital camera was developed to mimic the three cones found in the retina. In addition, an RGB camera's sensor optically couples to the target skin through a slight magnifier (<10×), and produces images that have a bit depth of 8 bits. This means that only $2^8$ (256) different brightness levels can be detected.

Hyperspectral dermoscopic images according to the present invention, however, are acquired by illuminating the skin with light emitting diodes (LEDs) at a plurality of different wavelengths sequentially for short duration (on the order of 100 ms). The resulting set of images yields more information about different features in the skin than RGB wavelengths, because the hyperspectral light interacts in a unique way with the complex biological structures found in the skin.

Additionally, more information may be obtained with the hyperspectral images, because the images are stored with increased "bit depth." Hyperspectral dermoscopy acquires images at preferably 4-50 wavelengths (an embodiment described herein uses 21 LEDs at distinct wavelengths) and each image has a bit depth of at least 12 bits. This means that at least $2^{12}$ (4096) different brightness levels can be obtained—sixteen times greater than conventional cameras. This increased bit depth results in a greater ability to resolve brightness differences within dark regions such as pigmented lesions.

The augmented spectral content available by acquiring images at, for example, 21 wavelengths instead of 3, has two advantages: the device can "see" colors outside of the visible spectrum such as the UVA and near infrared (nIR) ranges, and also distinguish colors that are too similar for the eye or the conventional RGB imaging sensors to resolve. Thus, hyperspectral dermoscopy has both a wider spectral range of imaging and better spectral resolution, which may result in enhanced detection of melanoma.

An exemplary array covering the hyperspectral range was constructed from commercially available LEDs having the following wavelengths, as specified by the manufacturer(s) ("λ spec"). In addition, the measured wavelength of the LEDs ("λ meas") were obtained with an onboard spectrometer, with the ability to feed the measured information to the processor. Although peak measured LED emission wavelength is provided in Table 1, the spectrometer is capable of measuring the entire spectral emission profile which may also be fed back to the processor to optimize operation and data collection.

TABLE 1

| LED | λ(spec) nm | Resistance Ohms | I_meas mA | λ(meas) nm |
|---|---|---|---|---|
| 1 | 361 | 100 | 30 | 364 |
| 2 | 375 | 22 | 25 | 374 |
| 3 | 385 | 39 | 24 | 386 |
| 4 | 400 | 22 | 24 | 396 |
| 5 | 405 | 39 | 20 | 400 |
| 6 | 440 | 33 | 24 | 434 |
| 7 | 470 | 100 | 14 | 466 |
| 8 | 490 | 56 | 24 | 488 |
| 9 | 507 | 56 | 16 | 508 |
| 10 | 525 | 100 | 14 | 518 |
| 11 | 557 | 56 | 27 | 558 |
| 12 | 571 | 56 | 22 | 571 |
| 13 | 590 | 56 | 25 | 593 |
| 14 | 610 | 82 | 23 | 610 |
| 15 | 630 | 82 | 26 | 632 |
| 16 | 645 | 82 | 26 | 655 |
| 17 | 680 | 0 | 32 | 677 |
| 18 | 740 | 56 | 33 | 740 |
| 19 | 770 | 18 | 34 | 766 |
| 20 | 850 | 82 | 22.5 | 843 |
| 21 | 940 | 22 | 20 | 934 |

The camera used for hyperspectral imaging may be a gray-scale camera or an RGB camera where the three color channels are added together to form one gray-scale image. The radiometric calibration enables specification of the fractional reflectance at any particular location in the imaging plane. Such a calibration is performed by obtaining an image with a calibration standard (e.g., Labsphere Spectralon diffuse reflection standard calibration target) and using said image in combination with the skin image and the relevant exposure information.

Figure 13:
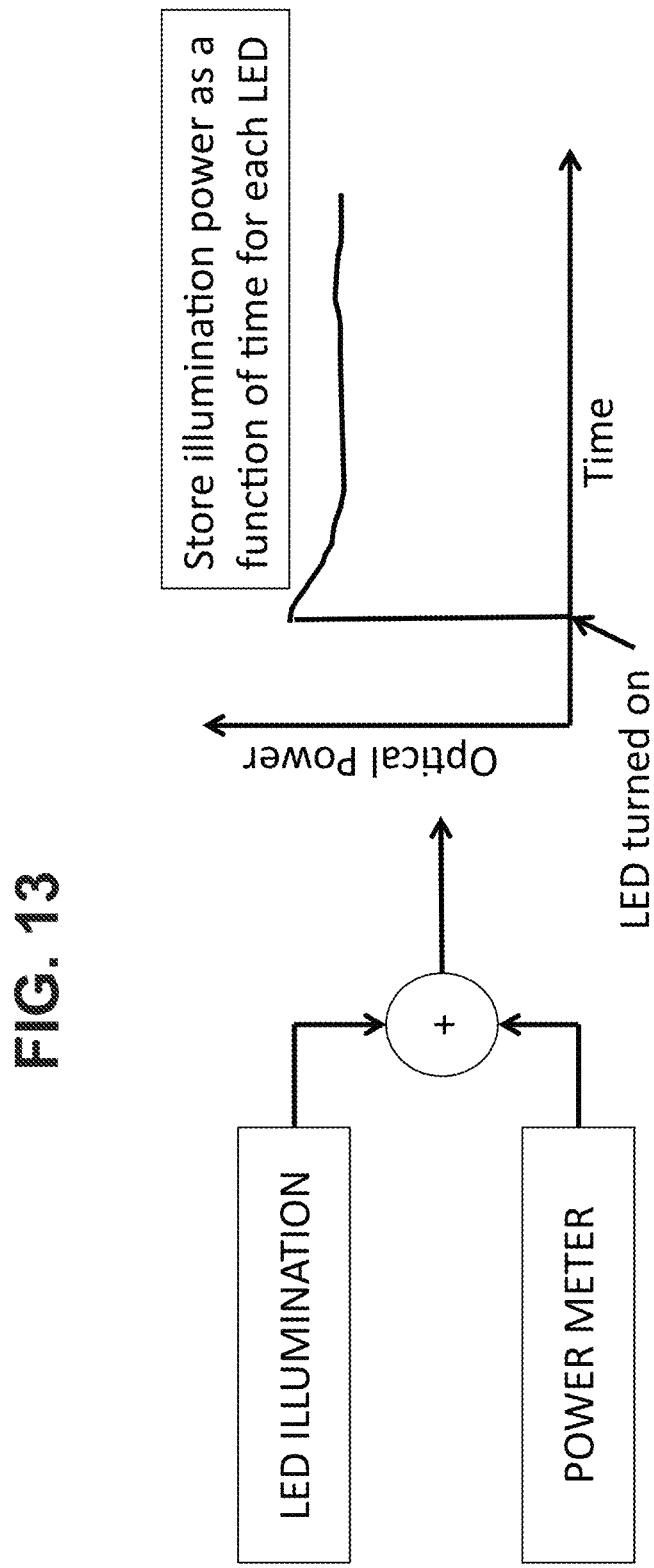
FIG. 13 is a flow chart depicting the acquisition of an optical power function for used for radiometric calibration of an apparatus according to the invention.

As shown in FIG. 13, radiometric calibration of the apparatus may be obtained by measuring and storing the optical illumination power of each LED as a function of time after turning on the LED. The system performance includes the optical power of illumination, which decreases slightly after turning on the LED. Normalization by exposure time alone is insufficient for calibration because an identical exposure time for a particular image using a particular LED wavelength may occur either immediately after the LED is turned on or at a later time, when the LED has been on for some time and the power is decreased.

Figure 14:
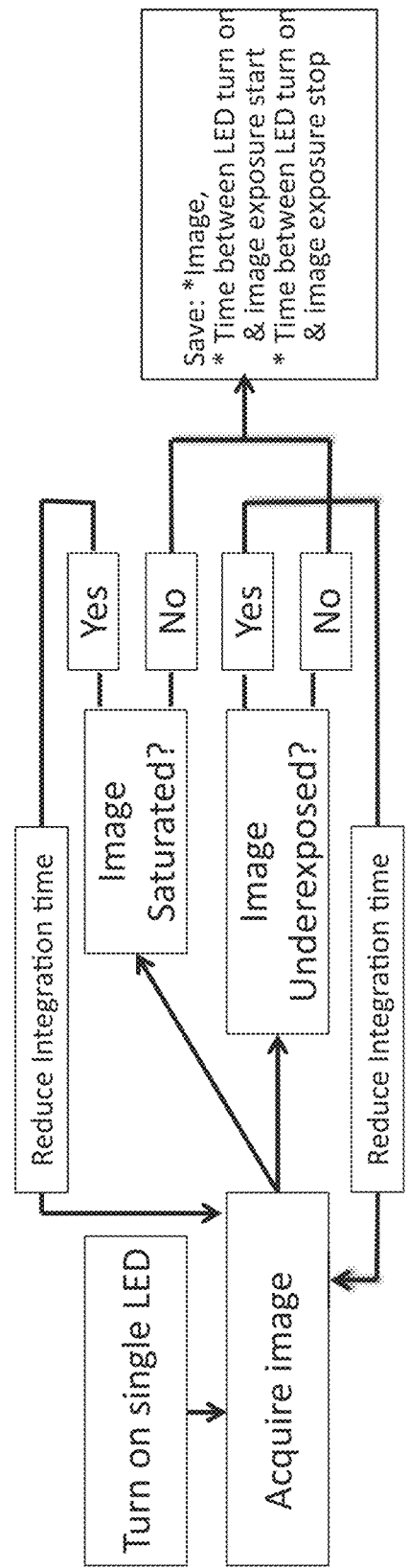
FIG. 14 is a flow chart depicting a data acquisition procedure in connection with calibrating an apparatus according to the invention.

To calibrate the apparatus, as shown in FIG. 14, sequential skin imaging occurs until the image is neither saturated nor under-exposed. If underexposed, the integration time is increased and another image is taken. If saturated, the integration time is decreased and another image is taken. This process repeats until a final image is taken that is neither under-exposed nor over-exposed, thereby exploiting the full dynamic range of the imaging system. At that time, when the final image is saved, the start times (A or C) and stop times (B or D) for the final image are registered with respect to the time when the illuminating LED was turned on.

Figure 15:
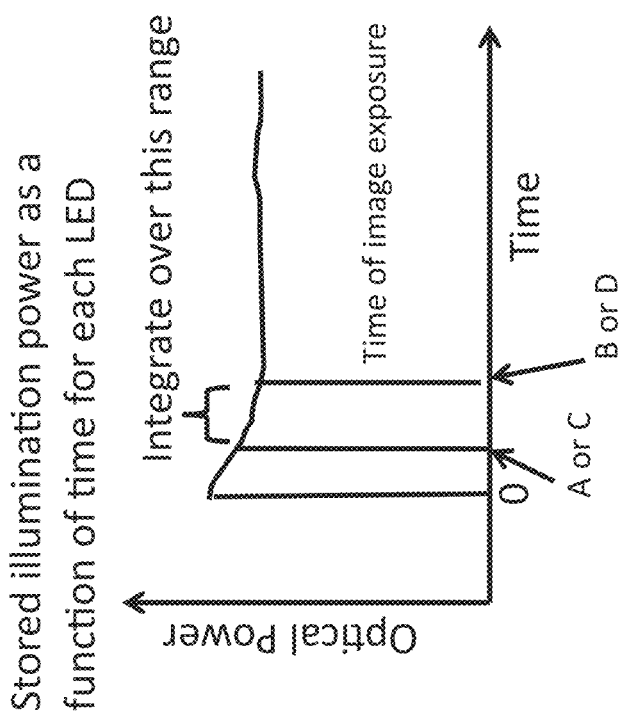
FIG. 15 depicts the procedure for radiometric calibration according to one embodiment of the invention.

As depicted in FIG. 15, this procedure yields an optical power calibration metric, which is the integral of the optical illumination power function, over the actual image exposure time from A to C (in the case of the standard image, resulting in the calibration metric C1), or from B to D (in the case of the skin image, resulting in the calibration metric C2.

In the embodiment of FIG. 1A and FIG. 1B, housing 101 comprises one or more lenses 121 mounted in the mechanical fixture 122 between the camera 13 and the distal imaging plane 12 to focus the camera on the distal imaging plane, and may comprise one or more filters, such as a polarizing filter or chromatic filter to condition the light emitted by the LEDs or reflected by the lesion and captured by the camera. The lenses are designed to minimize optical aberrations and maximize optical transport throughput at the wavelengths of the illumination light. The lenses are also designed to adjust the magnification of the optical imaging such that the field of view encompasses approximately twice the lesion size. In this manner, sufficient normal skin is imaged around the suspected skin disease but the magnification is increased as much as possible to obtain detail within the suspected skin disease.

In one aspect of the invention, means are provided to adjust the focal length of the lens system at different wavelengths of illuminated light to adjust for the different focal length of the lens at different wavelengths. A lens generally has a different refractive index at different wavelengths of light. A motor may be provided in a fixture between the sensor array and the skin lesion to move the lens system according to the wavelength of illuminating light. Under illumination of a particular wavelength an image may be processed to obtain a metric that measures the focal degree. This metric may be maximized to optimize the focus at the particular metric either in real time as the camera focuses or in post-processing to calculate the optimum position of the lens to obtain focus at the particular wavelength. This process may be repeated for each wavelength and the focal positions thereby determined may be stored to instruct the lens movement during skin imaging. In embodiments, the motor may receive programmed instructions to adjust the position of the lens according to the LED wavelength specified by the manufacturer of the LED. Alternatively, the motor may be programmed to position the lens system according to wavelengths of light measured at the lesion site with a spectrometer. The spectrometer may be a fiber optic element positioned near the site of the skin lesion.

The processing functions may be shared between first and second processors. The first processor is typically an onboard processor such as circuit board 11 adapted to drive the camera and illumination system to acquire the image data and provide real time information display to the user. The first processor may transmit image data to a second processor adapted to perform data-intensive processing functions which cannot readily be provided as real time display. The second processor may deliver messages back to the first processor for display. The second processor, if present, is typically a remote processor. The second processor may create data files, image files, and the like, for later use.

In the embodiment of FIG. 1A and FIG. 1B, in which the elements are shown schematically, the first processor is circuit board 11, adapted to drive the camera, focusing motor and illumination of the LEDs, while the camera sequentially obtains M images at the selected wavelengths. The first processor may process the image data so obtained to produce a display on a liquid crystal display ("LCD") view screen 19. Outer housing 191 encloses the LCD screen and circuit board. Cable 17 is used to attach a second processor and other components to the apparatus. Alternately, a battery onboard an apparatus according to the invention and antenna communications may be used to make the apparatus wireless As shown in FIG. 1A, fixture 100 is provided with a lens holder 102 attached to the nose cone by a spacer 103, sized to provide a self-contained assembly that can be manipulated with one hand and positioned against a subject's skin lesion.

Provided sufficient image data are obtained at different wavelengths, diagnostically relevant areas of interest on the skin lesion may be identified and differentiated using a variety of display modules. Thus, colors or hyperspectral signatures correlating to blood vessels within the lesion border; colors correlating to blue and blue white structures in the lesion; colors correlating to pigmented networks which may be regular or irregular; colors correlating to negatively pigmented networks; patterns of oxygen saturation; and patterns of eumelanin and pheomelanin (which have different absorption profiles) all may be highlighted and separately displayed with the display modules described below.

Figure 4:
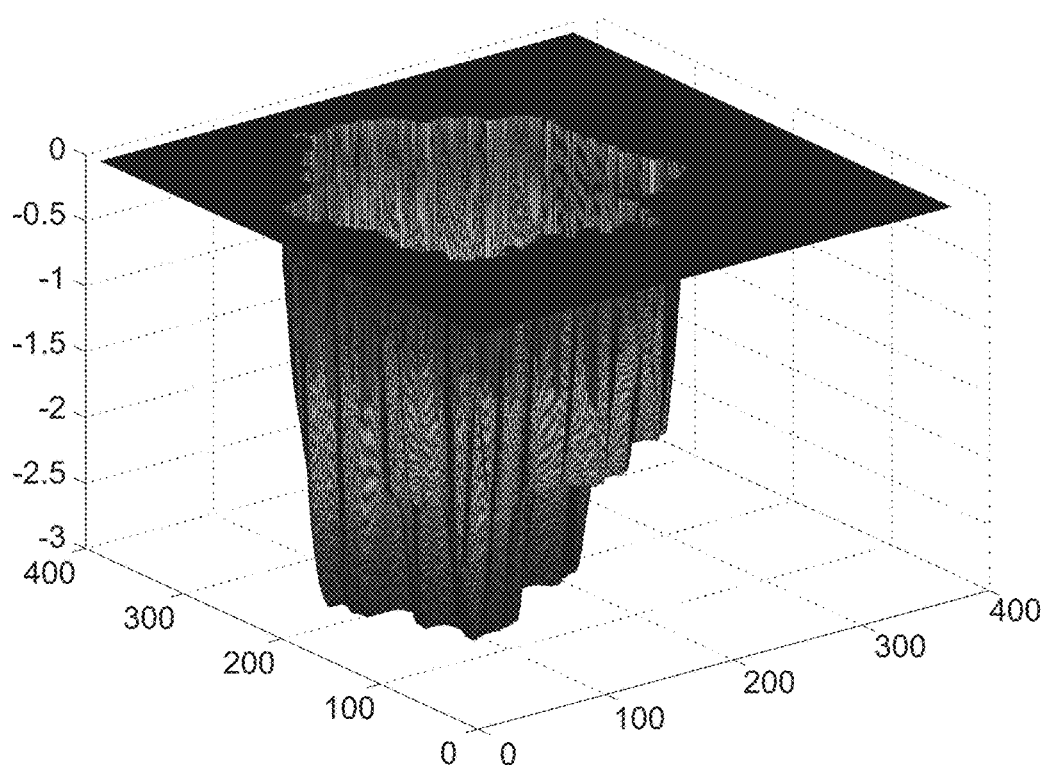
FIG. 4 is a topographical map of the depth profile of pigment in a lesion constructed from mask images according to a display module in one embodiment of the invention.

The processor(s) is adapted to transform the image data into diagnostically relevant metrics and/or one or more classifiers indicating the likelihood that skin disease is present in a lesion by defining one or more properties selected from the group consisting of [a] spatial texture features; [b] brightness features; [c] features of the edge/border; [d] color variation of a lesion on the subject's skin; [e] variations in the features of the pigmented network including the length, shape, brightness and organization of the pigmented network segments; and [f] oxygen saturation of the tissue defined by the amount and ratio of oxyhemoglobin and deoxyhemoglobin. These characteristics may be displayed in one or more display modules to render a version of the lesion image depicting the lesion, or segments of the lesion, with one or more of these features of interest highlighted on a display for the user. In one display module, depicted in FIG. 4, the N spectral images are processed to form a topographical map of the lesion pigment from mask images obtained at each of a plurality of specified wavelengths. A mask image is defined as an image having pixel brightness 1 inside the image border and 0 outside the image border. Image data obtained at each of the plurality of wavelengths will yield a different mask image with the masks of red/infrared images being typically smaller central regions of deeper pigment. Adding mask images at different wavelengths permits the construction of a topographical map that shows the lesion's depth within the skin. FIG. 4 is a black and white rendering of an original color image. This display module, which approximates a three-dimensional display, may be useful to identify the appropriate excision borders for a skin lesion or the ideal location of biopsy to most likely catch a malignant section of the lesion.

Figure 5:
FIG. 5 is a schematic view of a solid false color display according to a display module in another embodiment of the invention.

In another display module schematically depicted in FIG. 5, the N sequential images obtained by the camera are processed to render a display of the lesion in which areas of interest in the lesion are shown in solid "false color." The solid false colors in the display, for example, light brown, dark brown, red, black, blue/gray, and white, may be counted and the number of colors displayed. The solid false colors may correspond to detected regions of interest in the lesion, such as a region consisting of blood vessels within the lesion border; blue or blue-white skin structures a pigmented network that is labeled as regular or irregular; negative pigmented network (a connected pattern of lightly pigmented skin within the lesion borders); and an abnormal pattern of oxygen saturation as defined by spectral fitting using the M wavelengths of illumination. The display may toggle between a color image created from the M spectral images to be equivalent to what is seen with the eye, and the same image with a region or regions of interest indicated at the selection of the user. The highlighted features $R_1$, $R_2$, $R_3 \ldots R_n$ are depicted schematically in FIG. 5 as rectangles. In an actual embodiment, the shape of these highlighted features corresponds to the shape of the underlying feature in the skin lesion. The "false colors" in this display module do not depict the actual color of the region of interest, but are selected by the user to highlight the region of interest.

Figure 3B:
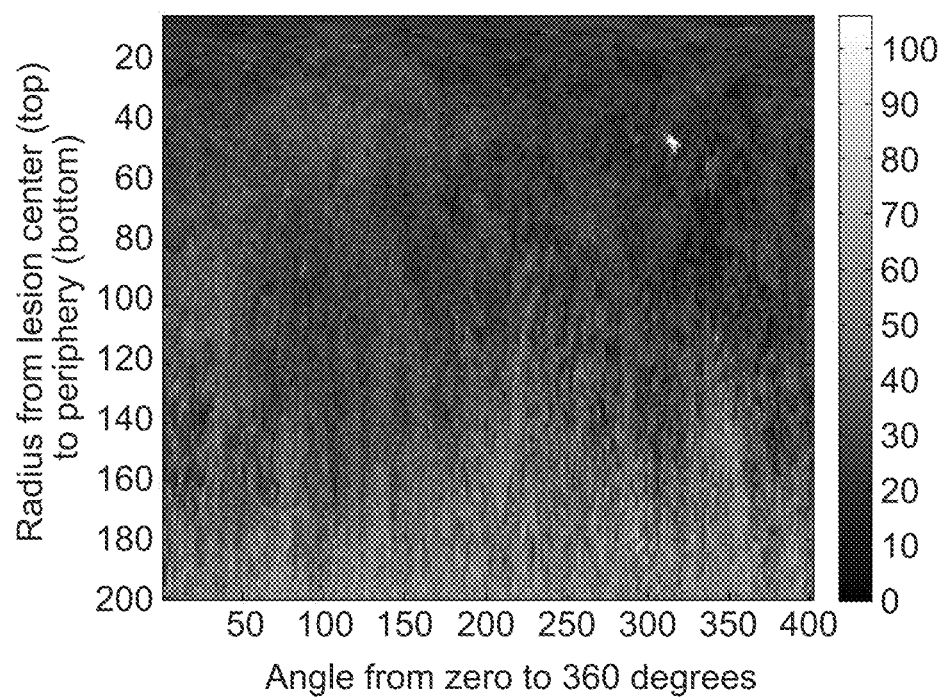
Figure 3C:
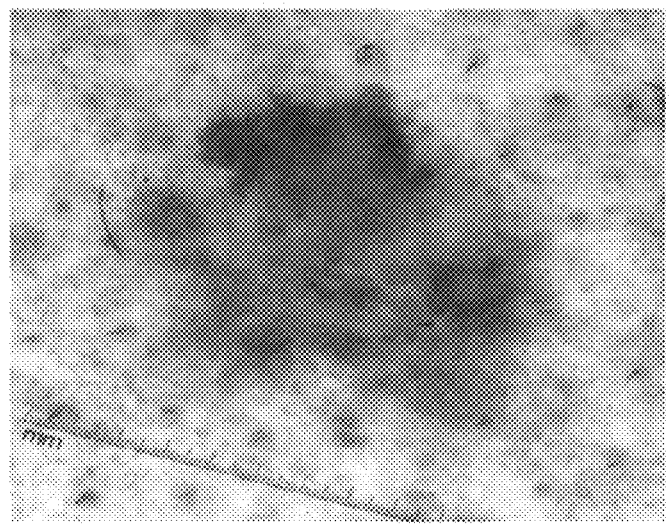
FIGS. 3C and 3D depict the polar transformation of image data for a malignant melanoma.
Figure 3D:
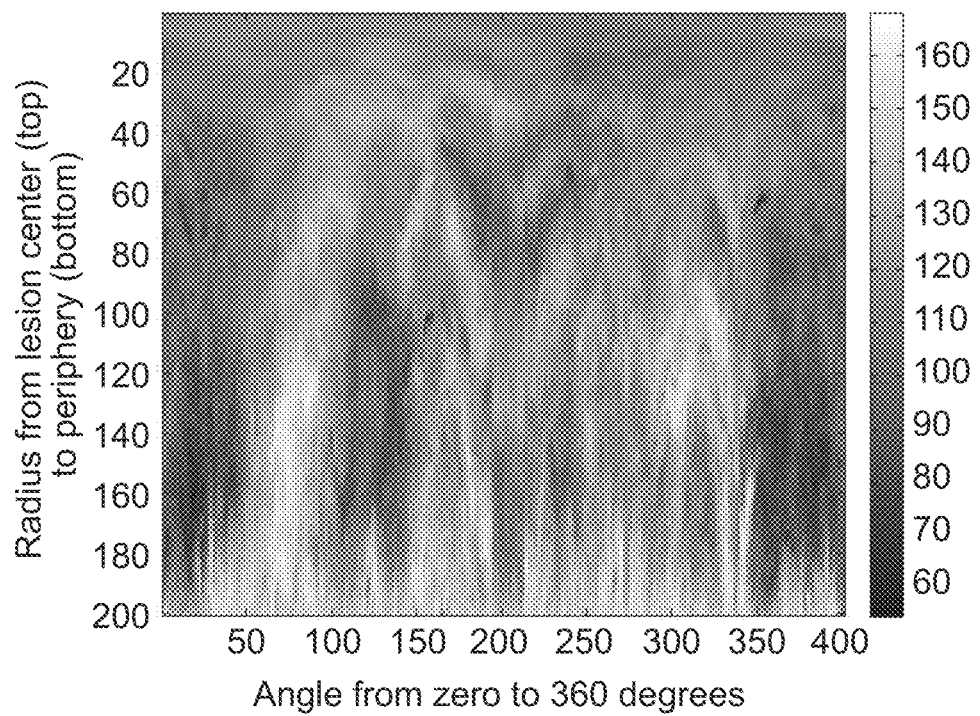

The display module of FIGS. 3A through 3D depicts the analytical advantage of the polar transformation of the visual data obtained from a skin lesion according to the present invention. FIG. 3A depicts conventional image data of a non-malignant skin lesion at a given wavelength. FIG. 3B depicts the polar transformation of the image data from FIG. 3A, in which the x-axis represents an angular position of the sweeping arm, and the y-axis represents the brightness values along the sweeping arm at each angular position. FIG. 3D depicts the same transformation of the image data from FIG. 3C, where the underlying image data is from a malignant melanoma. This display module provides a visual impression of the angular brightness variation in the malignant skin lesion to be read from left to right instead of rotationally, which is much greater than the variation in brightness of the non-malignant lesion. Even before quantitative evaluation, presentation of this image data in polar coordinates provides a new vantage to view a clinically relevant metric.

Figure 11:
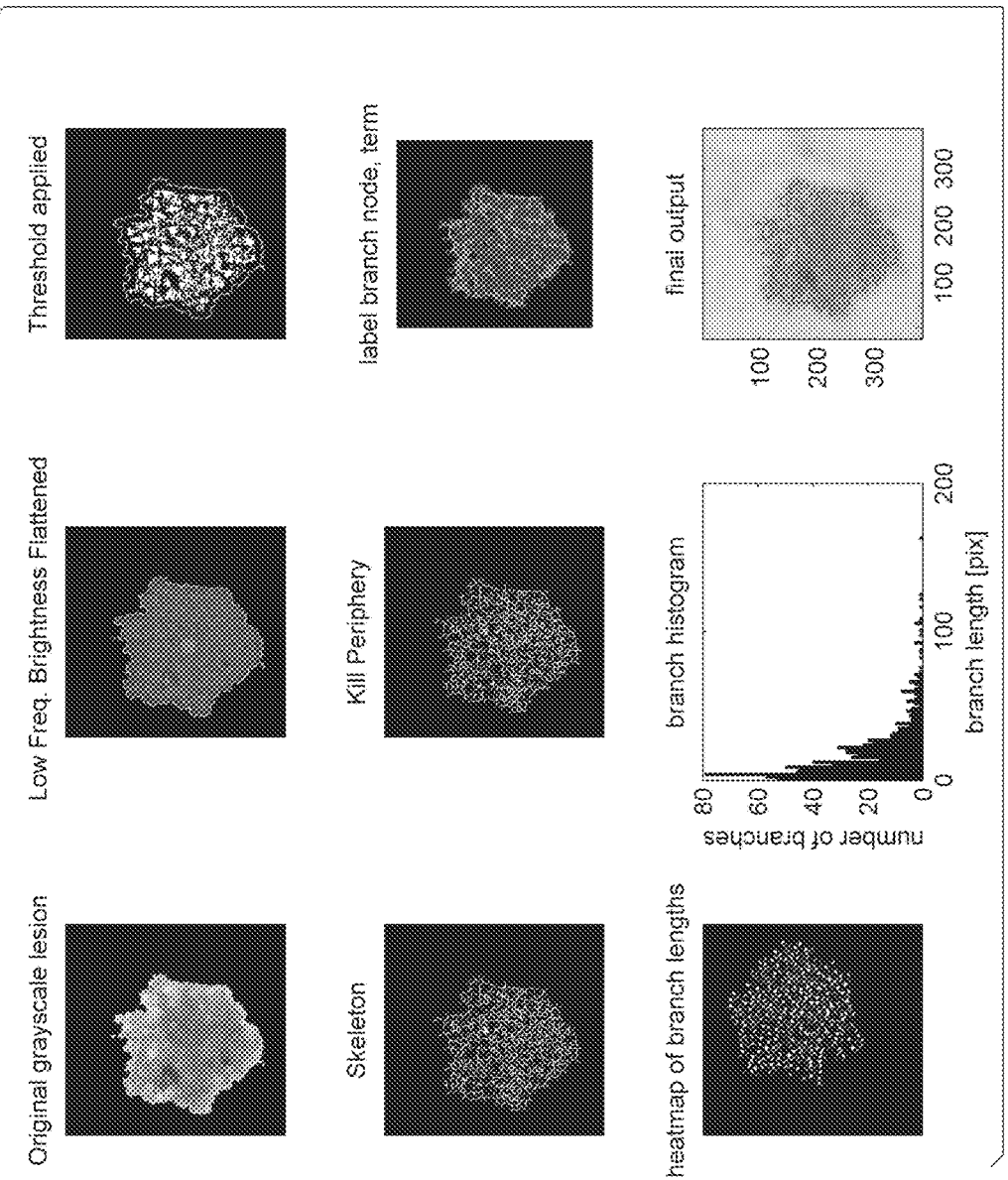
FIG. 11 depicts a transformative process performed on image data from a skin lesion to obtain a metric relevant to the pigmented network regularity in a skin lesion.

FIG. 11 depicts a series of data transformation steps which identify network nodes and branch segment lengths in skin lesion image data and provides a metric of network irregularity. In this context, "regular or irregular pigmented networks" refers to a measure of regularity defined by the branch segments of the network in terms of the length, width and brightness of each branch segment and the collective angular variation of those values. Important metrics are generated by identifying and characterizing pigmented networks from the image data, including the steps of: a) identifying branch segments; b) locating the coordinates of the centroid of the branch segment; c) determining the length and width of the branch segment and the ratio of length to width (or other mathematical combination of length and width); d) determining the brightness of the segment; e) determining the variation in brightness of the segment over different illumination wavelengths, $I\_L1$, $I\_L2$, $I\_L3 \ldots I\_Ln$; f) determining the number of nodes (where two branch segments meet), the number of ends, and the ratio of the number of nodes to the number of ends (or other mathematical combination of the nodes and ends). One such data transformation step which is helpful to resolve network nodes and branches is referred to as the "skeletonizing" step, as depicted in FIG. 11.

In identifying pigmented networks, especially to distinguish a pigmented network from a blood vessel structure, the variation in brightness across wavelengths is useful, because the blood vessel structure absorbs at different wavelengths than the pigmented structure.

The ratio of length to width is used to differentiate globular pigment patterns (where the ratio is closer to 1), from reticular patterns (where the ratio is much greater than 1). Variation in the ratio across the angular sweep produced is another metric correlated with melanoma.

A network includes branches connected by nodes and ends that are not connected to other branches. The ratio of the number of nodes to the number of ends produces a metric correlated with melanoma because a broken network (i.e., a lower node:end ratio) correlates to melanoma.

In addition to LCD viewer 19, the apparatus may comprise additional display outputs, adapted to display the M black-and-white or color coded scale images taken at M wavelengths as views in sequence or in a selectable manner, which may be facilitated by a server application between a computer and the data acquisition device. Data analysis of the multispectral imaging described herein was performed in the Matlab environment. However, transferring these program elements to a different programming platform is within the skill of one having ordinary skill in the art and this transfer is contemplated for commercial applications.

The camera may also be controlled with a server application that facilitates the image acquisition process and which can be operated independently or controlled through any separate software system capable of file input and output and simulating keystrokes. The server application acts as a bridge between the data gathering process and the data analysis code, to power the LEDs that illuminate the sample, to send image acquisition triggers to the camera, and to receive image information from the camera for data analysis in an efficient manner. The server application works by waiting for keystrokes (real or simulated) using a Windows message loop, which it then interprets and uses to send different commands to the camera. Additional data transfer between the server application and third party programs is accomplished using standard file input/output ("I/O") functions.

This server may be developed as a console application in C++ computer language, for example, with the ability to be re-implemented as a windows application, to handle image acquisition and changing resolution, exposure time and gains settings with the ability to add additional functionality as necessary. By enabling the server to be controlled by keystrokes, it can be used on its own to acquire images from the camera or in conjunction with third party applications that can simulate keystrokes. Total acquisition time for imaging 21 different wavelengths of light can be reduced to about 30 seconds or less (as opposed to around 60 seconds using software provided by the camera manufacturer). This server also enables a live feed display, enabling the user to position the assembly 100 around a suspicious lesion, for example, with a frame rate of at least 5 frames/second. Additional features may be included in the script to prevent accidental keyboard input from interfering with the server application while it is being controlled by a third-party application.

The functionality of the server application is enhanced by code that controls the lighting process, allowing for images to be taken at different wavelengths of light and with exposure times individually suited to each wavelength and as necessary, adjusted on the fly to prevent under-exposure or saturation, as well as code that enables the images to be displayed as a live feed either on a monitor or on a small screen attached to the imaging device.

Figure 10:
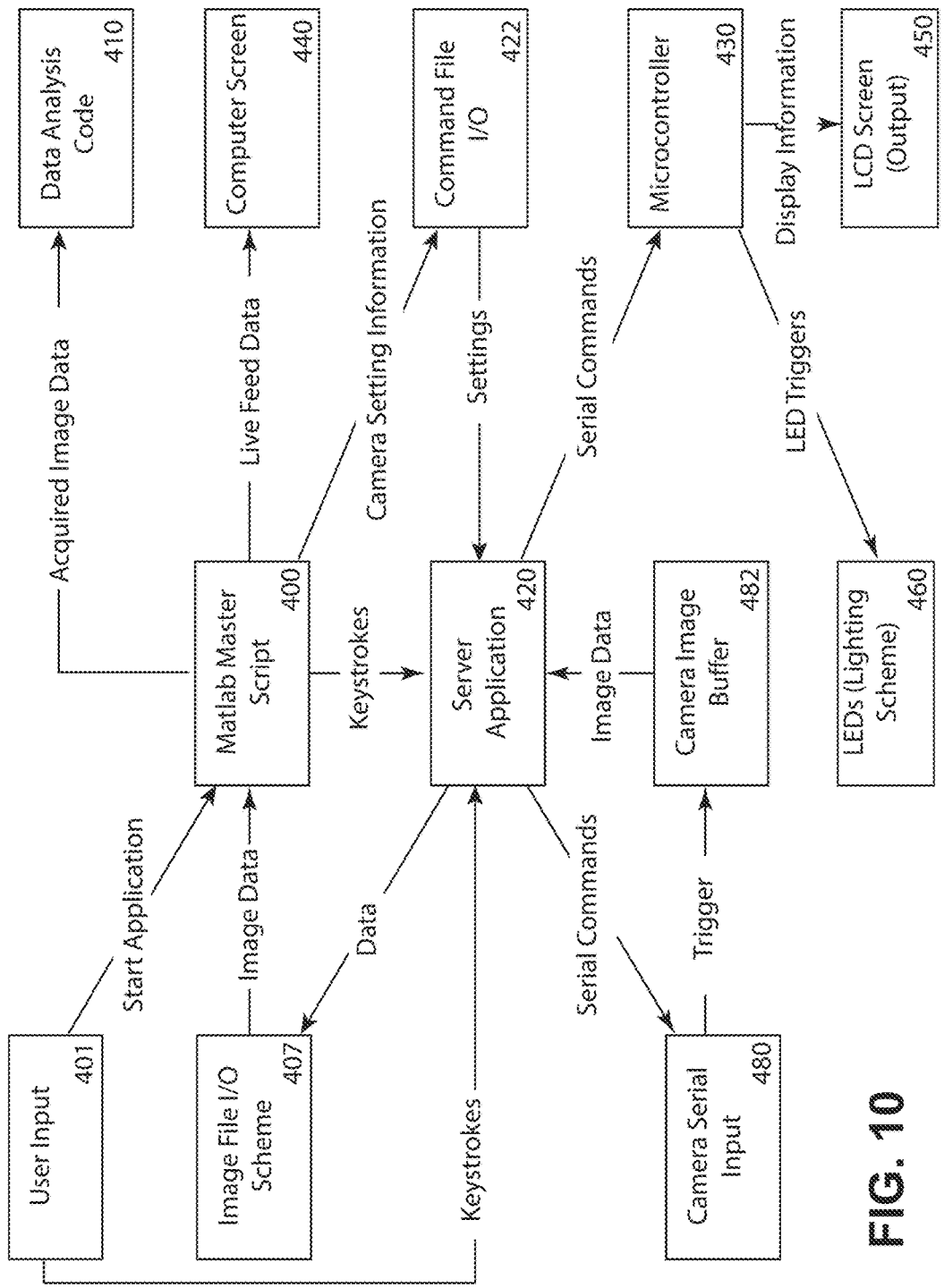
FIG. 10 is a flow chart depicting the operation of a server application controlling the image acquisition and data analysis process according to one embodiment of the invention.

The flow chart of FIG. 10 depicts the flow of commands and data acquisition and analysis using the server application. A master script 400 running on a first computer provides actual or simulated keystrokes to the server application 420, which controls image acquisition triggers through camera serial input 480 and then accesses camera image buffer 482 to return image data to the server application. The server application powers the LED array 460 through microcontroller 430. Once obtained, image data is processed by the master script in a data analysis code module 410. The server application 420 provides data to drive LCD screen output 450 and provides the master script 400 with live feed data for display on the computer screen 440 of the first computer.

Figure 17:
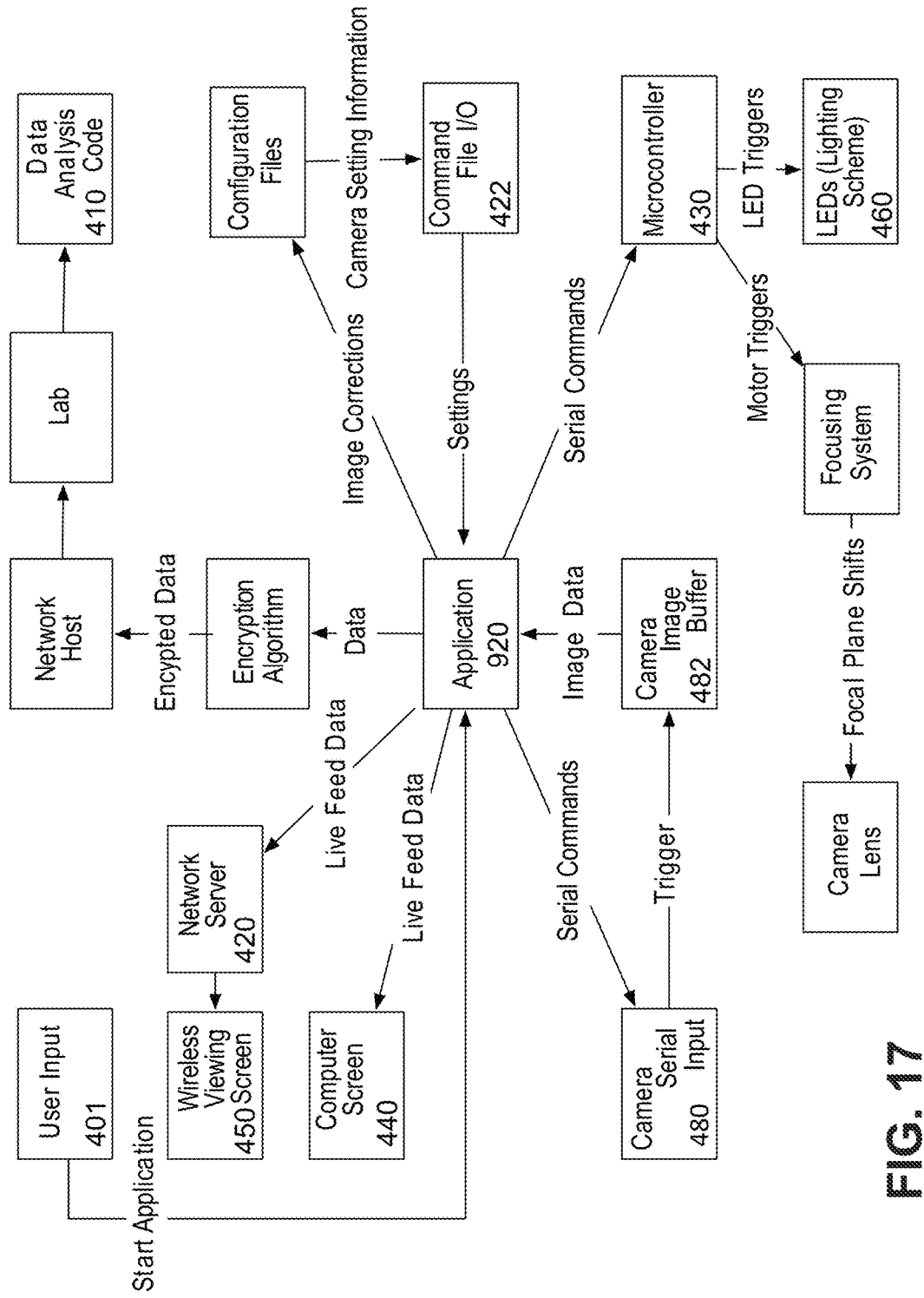
FIG. 17 is a flow chart depicting the operation of a server application according to another embodiment of the invention.

A refinement of the flow of commands and data acquisition is shown in FIG. 17, wherein application 920 refers to stand alone code (such as C++ code) that enables remote users to use an apparatus according to the invention—essentially master code that may be hardwired to enable commercialization of a standardized apparatus. The encryption algorithm enables secure transport of the data to a centralized analysis center where the diagnostic information can be rendered. A network host is the conduit for such data transfer. The lab refers to any central location where the data processing may occur. Alternatively, the functions may be provided onboard the apparatus: the analysis code would render the diagnostic information on the unit, like a smartphone application.

In the embodiment depicted in FIG. 2, the camera and processor are integrated in a cellular phone 20 (which includes "smart phones"). Many commercially available cellular phones have adequate camera capabilities and processing capabilities to implement the methods according to the invention. Cellular phones sold under the iPhone® and Android® brands, and many others, have the capability to download server applications to implement the methods described herein.

According to the embodiment of FIG. 2, a mechanical fixture 22 is attached to the cellular phone 20 so that the camera can be securely mounted while the fixture is positioned or pressed against the subject's skin. The distal end of the fixture 22 resembles a dermatoscope, and defines a plane 221 against which the subject's skin lesion is positioned or pressed to obtain an image while the camera is held in a fixed position. The fixture 22 may include an illumination system in the distal portion 223 of the fixture including an array of LEDs similar to the CCD camera embodiment described above, and/or polarizing or chromatic filter to enable partial rejection of the illuminating wavelengths or conditioning of the light received by the imaging camera. In this case, the fixture may be adapted to disable the camera's built-in flash. Alternatively, the processor may be adapted to utilize the built-in flash system provided with the cellular phone.

Figure 12:
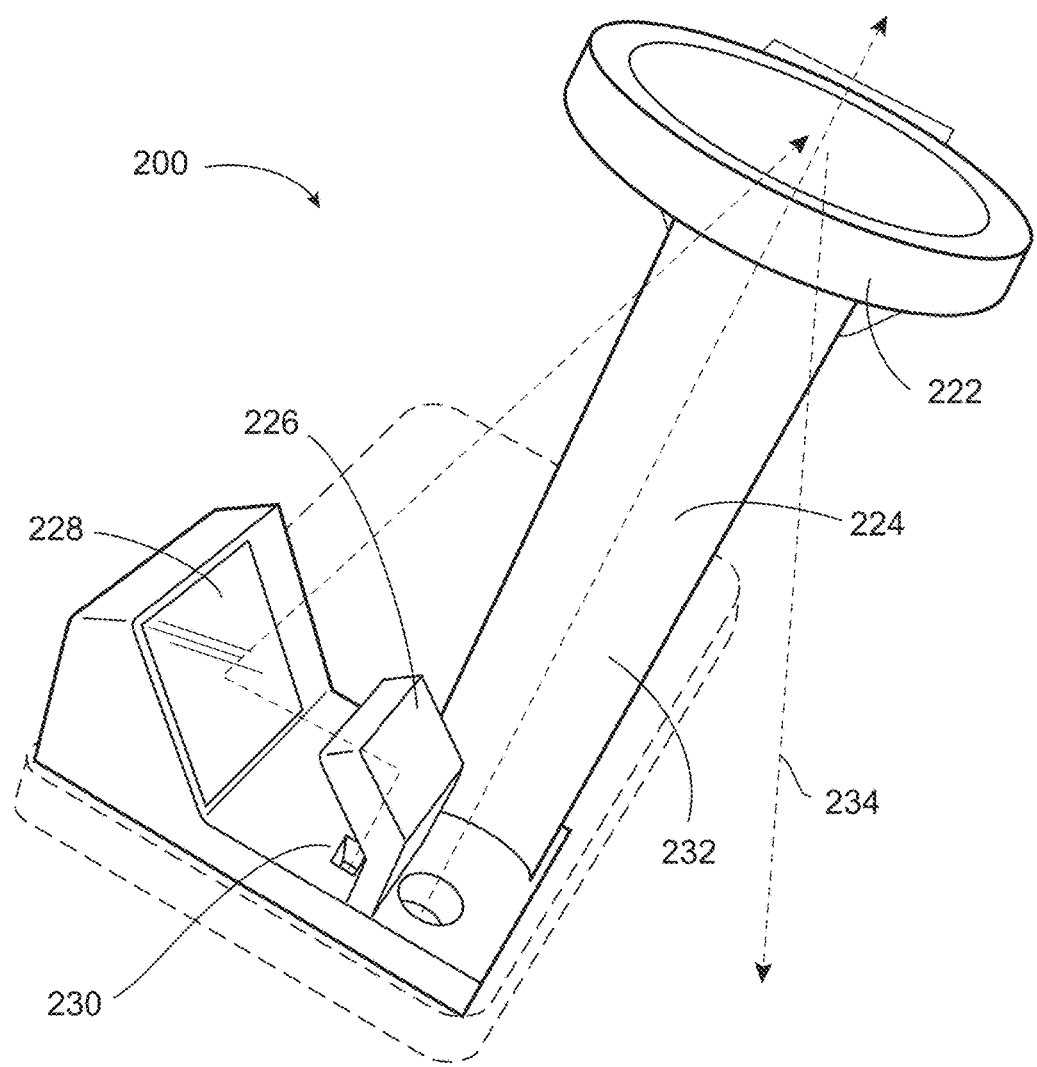
FIG. 12 depicts a mechanical fixture adapted to attach to a cellular phone and defining a distal imaging plane for positioning a lesion on a subject's skin with respect to the camera and attaching a mirror to direct light at a skin lesion on a subject's skin at an oblique angle.

In the embodiment of FIG. 12, the distal imaging plane is farther from the cellular phone camera lens, optimally leveraging the focusing and imaging capabilities of typical cellular devices. Fixture shaft 224 holds frame 222 several inches from the camera lens. Frame 222 is positioned or pressed against the subject's skin to define a distal imaging plane containing a lesion on the subject's skin.

Where the camera's built in illumination system is used to illuminate the lesion, a mirror may be used to direct light from the source to the surface of the lesion at an oblique angle, so as to avoid glare caused by reflection from the camera lens window. As shown in FIG. 12, a pair of mirrors 226, 228 may be attached to the cellular phone with a fixture, preferably capable of being temporarily attached to the cellular phone with a clip, adhesive, cellular phone sleeve, or the like. The fixture holding the mirrors may be combined with the fixture defining the distal imaging plane containing the lesion. A mirror may be used in tandem with a light filter, but in embodiments, the mirror is used without a light filter. In the embodiment of FIG. 12, a single fixture 200 is attached to the cell phone both for defining the distal imaging plane and for holding the mirrors for directing light at the lesion from an oblique angle. Light from the cellular phone built-in flash 230 is directed to the target at an oblique angle. Unwanted specular reflection from the target area (glare) is directed along path 234 away from the image path 232.

As with the clinical apparatus, external server applications may be adapted to drive the camera provided with the cellular phone and external illumination systems. The cellular phone or smart phone generally has a screen which serves as the output device which provides the user with an indication that a skin lesion is melanoma. The output may take the form of a percentage likelihood that a skin lesion is melanoma, together with a percentage uncertainty, or the program may provide the user with a qualitative message, such as "suspicious lesion: see your dermatologist."

In another embodiment, the invention combines wide and narrow field of view imaging systems for effectively delivering the technology to the end user, i.e., patients, doctors and the public. This combination may include a first illumination system for illuminating a first area on a subject's skin; a camera having a wide field of view for obtaining wide field image data from the illuminated skin; a processor for processing the wide field image data to obtain a target area within the first area which includes at least one skin lesion; a second illumination system for illuminating the target area; a camera having a narrow field of view for obtaining narrow field image data from the illuminated target area; and a processor for processing the narrow field image data to obtain diagnostic information pertaining to the at least one skin lesion. The wide field image data can be processed with rotational analysis using the clock-sweep algorithm described above, or other techniques may be employed to identify a target area containing a lesion on the subject's skin. Narrow field image data may then be obtained from the target area with a camera having a second field of view narrower than the field of view of the first camera, using a second illumination system.

The wide field of view is intended to image a relatively large portion of a subject's skin, potentially containing plurality of skin lesions ("target areas" or "areas of interest") for further evaluation. Areas of interest, such as a skin lesion, are identified in this wide field area and then isolated, for example, by adapting techniques and apparatus for facial photography described in U.S. Pat. Nos. 7,603,031, 8,218, 862, and 8,498,460, referenced above. Alternatively, wide field image data may be obtained with a cellular phone or smart phone. In still another embodiment, a wearable computer, capable of projecting images to the wearer with interactive processing capability, is well suited to obtain the initial wide field image data according to this aspect of the invention. In preferred embodiments of the invention, the wide field image data is processed to obtain statistical evaluation of the size and irregularity of lesions in the first area.

In this aspect of the invention, narrow field image data may be RGB image data obtained with a conventional smart phone camera, or more preferably, hyperspectral image data obtained and processed using the apparatus, methods and systems described above. That is, after a lesion is identified, a camera adapted with an illumination and sensor array for hyperspectral imaging processes the image data with a clock sweep algorithm to obtain diagnostically relevant metrics and/or one or more classifiers defining the rotational symmetry on a per lesion basis from the rotational distribution of properties selected from the group consisting of: [a] spatial texture features; [b] brightness features or [c] features of the lesion image edge/border, including the sharpness with which the lesion borders normal skin; [d] color variation of a lesion on the subject's skin; [e] variations in features of a pigmented network including the length, shape, brightness and organization of pigmented network segments; and [f] oxygen saturation of tissue as defined by the amount and ratio of oxyhemoglobin and deoxyhemoglobin. This group of properties may also include [g] the heterogeneity of pigment species such as eumelanin, pheomelanin and other species of pigment.

Thus, successively more sensitive and selective diagnostic indications are obtained, first on the meter scale, with a wide field image data acquisition system, and thereafter on the centimeter scale with narrow field image data. When a target area is identified in the wide field image data, the narrow field image data processor is able to locate a center and border of the lesion and determine that the lesion is in fact the target area.

Successively finer resolution imaging systems may be used to provide increased diagnostic sensitivity and selectivity. For example, after a lesion is evaluated with the narrow field image data processing and an indication of the likelihood of the presence or absence of skin disease is obtained, the clock sweep algorithm may be applied to more finely resolved image data, for example, image data obtained with a confocal microscope. The identified lesion, or a target area within a lesion, may be evaluated with a still finer resolution image acquisition system, such as a Raman spectroscope.

Methods, Metrics and Classifiers

Figure 16:
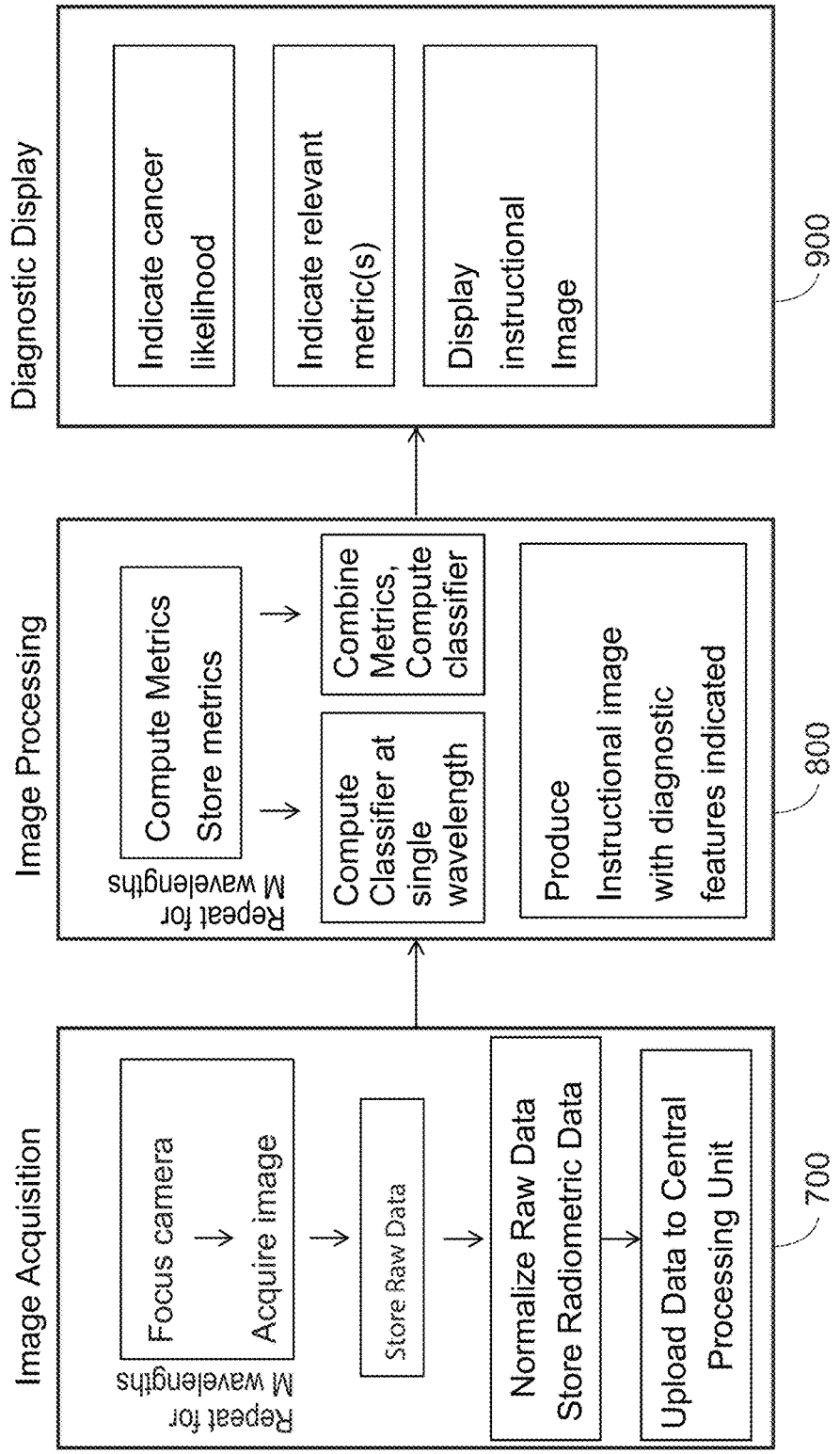
FIG. 16 is an overview of the image acquisition, image processing and diagnostic display components of the invention.

The methods according to the invention may be described as a series of conceptual "steps." As would be apparent to the person of ordinary skill in the art, the steps may be followed sequentially, or in an order different from the order stated; the steps may be done in parallel, done at the same time, or done iteratively, without departing from the scope of the invention. Describing a step as the "first step" or "next step" is for convenience only. The image data obtained from a subject's skin lesion may be manipulated by computer according to these steps and output to display modules. FIG. 16 depicts an overview of the image acquisition 700, image processing 800 and diagnostic display 900 processes that are described herein.

The first step of the method consists of obtaining image data from a subject's skin with a camera. Generally, this means photographing a lesion on the skin. The resulting image data will comprise data from the lesion and the surrounding skin, and may include data which are not part of the lesion or surrounding skin, including hair, markings made by a dermatologist or other data elements that are not analyzed and simply need to be removed from the image. To complete this step, the processor may replace pixel brightness and color values of the hair-containing locations with pixel brightness and color values of the skin underlying or immediately adjacent the hair, for example.

The image data consists of pixel gray-scale or brightness information in M different color layers. As used herein, a "multispectral image" is an image obtained at a plurality of wavelengths or "layers," so that each pixel in the image is associated with M numbers that form a spectral measurement, and each in, is a brightness or gray scale measurement at a different color layer. Thus, the image data consists of M images sequentially acquired by the camera while illuminating the skin at wavelengths that range from 300 nm to 950 nm. The spectral measurement is fit as the weighted sum of N chromophores, corresponding to the number M of images obtained. Typically, pixel brightness information is obtained at least in the red-green-blue ("RGB") layers, but pixel brightness information is also preferably obtained for other spectral bands. Relevant information is obtained using illumination and detecting reflected light in the visible and non-visible range, including the blue and UV range at 300 nm to 500 nm, and even more particularly in the non-visible 300 nm to 400 nm UV range.

As used herein, "chromophores" refers to color components found in a skin lesion, such as melanin (including eu-melanin distinct from pheo-melanin), oxygenated hemoglobin and deoxygenated hemoglobin. Generally, at least these four have distinct absorption profiles such that the spectral images can be analytically fit as the weighted sum of at least these four chromophores. However, skin contains water, which absorbs in the infrared, bilirubin, which has a distinct absorption in the visible spectrum, and potentially could be found to contain other diagnostically relevant components, such that a measurement could be fit as a weighted sum of N chromophores, wherein N is 4, 5, 6, or more chromophores.

Once the image data is obtained, the border, shape and center of the lesion are identified. The first step in determining the shape is known as "segmenting" and various computer implemented techniques known in the art may be used to identify the shape and border of a lesion. Briefly, segmenting results in a mask being applied so that pixel brightness at a given wavelength is reduced to a mask image, in which pixels have brightness value of 1 inside the lesion and 0 outside the lesion. A "mask" as used herein is an image having a brightness value of 1 inside the image border and 0 outside the image border.

In a subsequent step, the center of the lesion (or close approximation of the center) is determined. The center of the lesion may be calculated as the center of mass or geometric centroid of the mask image, such that each region of the lesion shape is treated as having identical density. Alternatively, the center of mass may take into account the variation of brightness in the shape. Unless stated otherwise, in the following examples, the center of mass is obtained from a mask image, such that the lesion is treated as having uniform brightness to determine the center of mass. As the image will have a different mask and therefore a different border at each wavelength, the image at each wavelength may be associated with a respective center, and the distance between the "centers" ("$\Delta r$") may be used with other metrics. The variance ("var $\Delta r$"), range ("range $\Delta r$") and mean ("mean $\Delta r$") may also be combined into classifiers.

Figure 7:
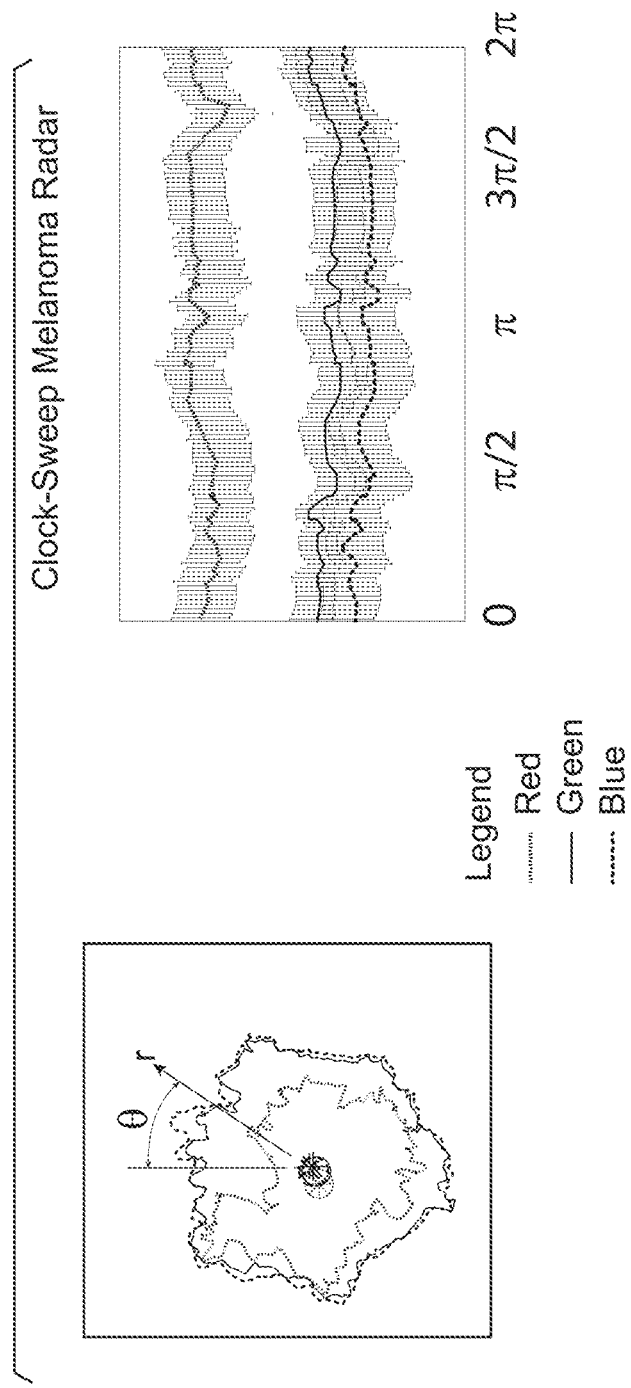
FIG. 7 depicts another display module according to the invention where the lesion borders are indicated on the left for each of the color channels, and on the right, the angular brightness function is plotted for the color channels.

A sweeping arm is a line segment connecting the center of the lesion to the border. The "clock-like" sweep as used herein, means rotating the sweeping arm about the fixed center of the image in either a clockwise or counter-clockwise direction to obtain information about the pixels on the sweeping arm as a function of rotation angle. To obtain metrics from the image data, the sweeping arm rotates around the center with one end fixed at the center for 2 pi ($2\pi$) radians or 360° (one complete sweep). Data is sampled at regular intervals of radians or degrees. FIG. 7 depicts the clock sweep arm r at an angle $\theta$ with respect to the vertical. On the left hand side of FIG. 7, borders of the lesion at three different wavelengths are shown. On the right hand side of FIG. 7, the brightness of the pixels on the sweeping arm is plotted as a function of angular position. The data obtained in the sweep may be processed into a series of metrics and/or one or more classifiers which cannot be obtained by evaluation of image data which have not been transformed into polar coordinates.

As used herein, "metrics" are values calculated from the image data which bear a correlation to disease states (melanoma in the preferred examples). Examples of metrics are listed in Table 2.

TABLE 2

| V1 | Angular brightness range |
|---|---|
| V2 | Mean standard deviation (S.D.) of brightness |
| V3 | Range in S.D. of brightness |
| V4 | Standard deviation (S.D.) of S.D. in radial brightness over all angles |
| V5 | Mean absolute brightness shift between successive angular positions |
| V6 | S.D. of absolute brightness shifts |
| V7 | Sum of the brightness shifts over full sweep |
| V8 | Maximum border asymmetry |
| V9 | Border asymmetry evaluated at 90° with respect to the minimum asymmetry axis |
| V10 | Lesion border length/lesion area |
| V11 | Mean lesion demarcation (edge slope) |
| V12 | S.D. of lesion demarcation |
| V13 | Fractal dimension |
| V14 | Lesion brightness variation over all lesion |
| V15 | Mean demarcation (edge slope) fit error |
| V16 | S.D. demarcation (edge slope) fit error |
| V17 | Lesion brightness variation over all lesion |
| V18 | Mean length/area of pigment segments |
| V19 | S.D. length/area of pigment segments |

Metrics V1 through V7 and V14 capture measurements and statistical information relating to the variation in brightness of pixels on the sweeping arm in relation to other pixels on the sweeping arm, and over different angular positions of the sweeping arm. Metrics V8 through V13 and V15 through V19 capture measurements and statistical information relating to the edge characteristics and presence of reticulated structures in the lesion.

The metrics enable quantitative analysis of parameters familiar from conventional dermatological examination, such as the ABCD technique of lesion screening, which evaluates the asymmetry (A) of a lesion, and lesion border (B), color (C) and dermoscopic structures (D). But the systems and methods of the invention also provide a wealth of information that cannot be obtained from conventional screening, ultimately yielding a percent likelihood that a lesion is melanoma or nevus, which conventional screening could never do. According to the invention, the factors relevant to conventional dermatology are synthesized in a series of metrics, which are then combined in one or more classifiers that may be trained on a set of lesions of known pathology to yield a system of diagnosis of skin disease.

One metric that may be obtained from the angularly sampled data is the angular brightness range (V1), defined as the maximum value of mean brightness on the sweeping arm minus the minimum value of mean brightness over the full rotational sweep. Thus, the mean brightness of the pixels on the sweeping arm is calculated at each angular sample position of the sweeping arm, and the minimum value calculated is subtracted from the maximum value to obtain (V1). The angular brightness range (V1) will vary more if the lesion has overall non-uniformity in pigment.

The right hand side of FIG. 7 depicts the angular brightness range of pixels on the sweeping arm (V1) as a function of angular position. The mean standard deviation of brightness (V2) of pixels on the sweeping arm is depicted as the vertical line associated with each angular position. Large variations in (V1) and a large range of (V2) correlate to melanoma. For the mean standard deviation of image brightness (V2), the variance in angular brightness as calculated with the standard deviation reveals an additional feature of oscillating brightness around the angular sweep. If the brightness alternates between light and dark many times over the sweep, this variable will be larger, whereas the angular brightness range (V1), will only pick up the peak to minimum brightness range.

Another metric that may be obtained is the range in standard deviation of brightness (V3). A standard deviation is obtained from all the values of brightness on the sweeping arm at each angular position and the range of these values over all angular positions is calculated to obtain (V3). For the standard deviation of the values of variance along a single instantaneous radial brightness over all the possible angles (V3), the individual standard deviations are plotted as vertical black lines. The mean standard deviation of the radial brightness is evaluated over all angular positions. This variable (V3) measures the variation of brightness along the radial clock arm that sweeps the lesion. Though this variable (V3) will be higher for heterogeneous pigment distribution, it does not distinguish between globular and reticular pigmented patterns.

Another metric is the standard deviation over all angles of the standard deviations at each angular position (V4). This variable describes to what degree the heterogeneity of pigment distribution itself is heterogeneous. This variable (V4) would be high, for example, if there were some angles at which the lesion contained an even pigment distribution and other angles that contained a reticular or globular pattern of bright/dark areas.

Other metrics evaluate the brightness shift (absolute value) at successive angular positions (V5) the standard deviation of the absolute value of the brightness shift over all angular positions (V6), and the sum of the brightness shift (absolute value) over all angular positions (V7). The mean instantaneous brightness shift at successive angular positions (V5) is the average derivative of remittance of the angular brightness over all possible angles. The average derivative of remittance adds up the instantaneous changes in brightness over all possible angles, in this way, the variable (V5) is similar to variable (V2). The standard deviation of the absolute value of the brightness shift over all angular positions (V6) is the derivative variance. The variance of the derivative of remittance describes how much variability exists in the instantaneous change in brightness over the angular sweep. If some angular ranges are flat (i.e. low intra-range brightness derivative) and some ranges vary wildly, the variable (V6) will have a high value. The sum of the brightness shift over all angular positions (V7) is the total variance. For a uniformly colored lesion, the variable (V7) is zero.

The person of ordinary skill in the art of computer-implemented diagnostic analysis of dermoscopic images will recognize that the angularly sampled spectral image data lend themselves to mathematical combination and statistical manipulation once the data is obtained, so that the foregoing list of metrics having correlation to disease states is not exhaustive.

Figure 6:
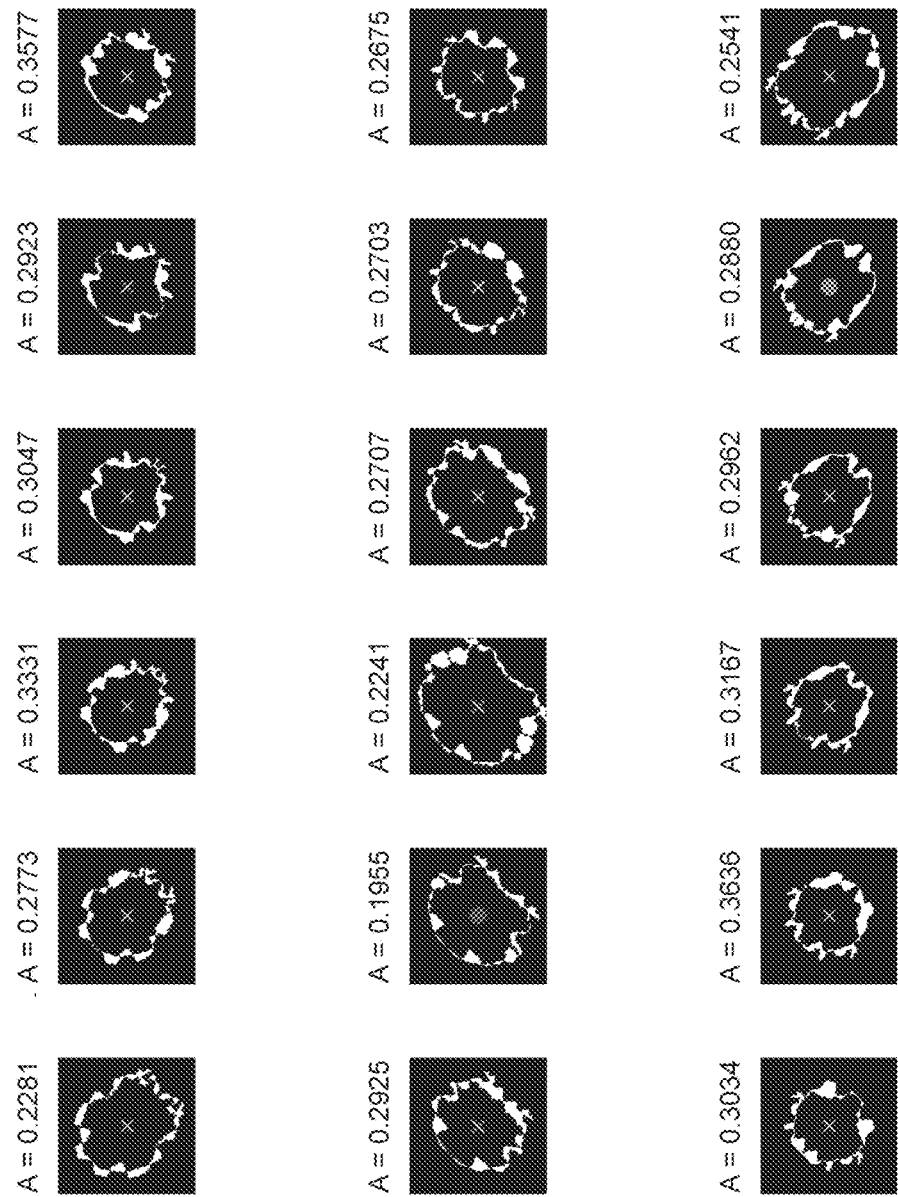
FIG. 6 depicts asymmetry measurements obtained with respect to bisecting axes which are rotated with respect to the image, where a circular dot is plotted in the center of the lesion at the angle where the symmetry is maximum as indicated by the minimum value of mismatched area (A=0.1955) and the symmetry is evaluated at 90-degrees from this angle with a second circular dot (A=0.2880).

The maximum border asymmetry (V8) is another metric, along with the border asymmetry perpendicular to the axis of most symmetry (V9). The border asymmetry is calculated by flipping the silhouette of the lesion and dividing the mismatched area by the total area. An irregularly shaped border will result in a high value for this variable (V8). In embodiments, border asymmetry was obtained by converting the lesion segment in the blue channel to a binary mask and flipping the binary lesion about a bisecting axis, thereafter rotating the axis in 10 degree increments from zero to 180 degrees to obtain 18 samples of asymmetry as a function of analysis axis. The subtraction of the original mask from its flipped counterpart yielded a map where overlapping regions had a zero values (1−1=0), regions not occupied by either the original or flipped mask had zero values (0−0=0) and regions of mismatch had an absolute value of 1 (1−0=1 or 0−1=−1). The absolute value for a perfect circle would be zero everywhere and the sum would be zero, indicating perfect symmetry. Real lesions had mismatched areas, which lead to non-zero values in the subtraction map, which when summed and divided by the sum of just the original mask, equaled the fractional area of mismatch, and represented the asymmetry of the border of the lesion. The angle at which the minimum asymmetry factor occurred was designated as the axis of most symmetry. Then, the asymmetry of the lesion was evaluated at 90 degrees with respect to the symmetry axis. The individual asymmetry images are depicted in FIG. 6. The border asymmetry perpendicular to the axis of most symmetry (V9) is similar to variable (V8), but instead of reporting this variable when flipping the lesion about the axis that yields the highest value of the variable, variable (V9) reports the result using the axis perpendicular to the axis that yielded the lowest value of the variable.

Some of the metrics obtained from scanning and analysis of the pixel brightness information are obtained for a given wavelength. Other metrics require a combination and/or comparison of image data obtained at different wavelengths. Regions of interest in a lesion may be associated with different colors, including blood vessels (red) within the lesion border, blue or blue-white skin structures, pigmented networks (associated with eumelanin (brown) or pheomelanin (red).

The border roughness metric (V10) is the length of the border of the lesion segment squared divided by the area of the lesion. For a circle, this would be the circumference squared divided by the area. The border roughness (V10) describes how much the radius of the lesion varies during the clock sweep scan of the lesion. For a circle, the variable will be minimized but for a lesion that has many fingers protruding into the normal skin, this variable (V10) will be high.

Initially, the clock sweep may be used to enhance the determination of the border. An edge fit algorithm runs during the clock sweep and utilizes the variation in pixel brightness at the edge of the lesion shape to iteratively determine a more accurate edge.

The "edge slope" metric (V11) is the mean gradient in brightness at the border during the transition from dark (inside the lesion) to light (outside the lesion) over the full sweeping arm rotational range. Also characterized as the edge slope or edge sharpness (V11) quantifies lesion demarcation. If the lesion has an abrupt border, as in melanoma, this variable (V11) will have a high value. The standard deviation of edge slope over all angular positions produces the standard deviation of lesion demarcation (V12). For the standard deviation of the lesion demarcation (V12), the variation in the edge sharpness will be high if the lesion border in some locations is sharply demarked and in other locations is a more gradual transition. An edge fit algorithm may be used to produce a function defining the border of the lesion from the edge slope which also produces edge slope fit error (V15). An edge slope fit error for the standard deviation of lesion demarcation (V16) may be similarly obtained. The fractal dimension (V13), The fractal dimension (V13), which can be a Hausdorf fractal dimension of the lesion silhouette at a particular wavelength is another measure of the border irregularity which may be calculated according to known methods. The length to area ratio of pigment segments (V18) and standard deviation of this ratio (V19) are also metrics which bear correlation to melanoma.

Additional metrics include variables (V20) through (V30). The ratio of the mean diameter of the lesion segment to the maximum correlation distance (V20) describes the size of the pigmented network features relative to the size of the lesion. For a lesion with small pigmented features such as a well-defined reticular pattern, this variable (V20) will be high while for a lesion that has large areas of dark pigment such as globules, this variable (V20) will be low.

The eccentricity factor of the cross correlation matrix of the lesion segment image (V21) is the ratio of correlation in X to correlation in Y. This variable (V21) quantifies asymmetry in the cross correlation of the lesion. If a lesion has long pigmented ridges, for example, the correlation length along the direction of the fingers will be high while the correlation length perpendicular to the fingers will be small. Such a lesion will have a high value for this variable (V21).

The standard deviation of the lengths of the pigmented network branches in the entire lesion (V22) is another metric. For the branch analysis, which skeletonizes the pigmented network, this variable (V22) quantifies the variability in branch lengths. If the lesion has some areas with many small branches but other areas with long branches, this variable (V22) will be high.

The standard deviation of the brightness of the pigmented network branches in the entire lesion (V23) is another metric. If the branches have variable intensities (i.e. some branches are dark and some are light), this variable (V23) will be high.

The mean value of the standard deviation in branch brightness over the mean branch brightness, over all the branches (V24) describes the intra-branch variability in intensity.

The average eccentricity of the original dark network segments (long axis diameter divided by short axis diameter) (V25) describes how elliptical the original (un-skeletonized) pigmented regions are. If the pigmented regions are natural branches such as in a reticular pattern, this variable (V25) will be high. If the pattern is globular and the pigmented regions are more round, this variable (V25) will be low.

The standard deviation of the eccentricity of the original dark network segments (long axis diameter divided by short axis diameter) (V26) quantifies the variation in elliptical factors of the pigmented regions. If a lesion has a globular component as well as a reticular component, this variable (V26) will be high.

The connectedness of the pigmented network (V27) is the number of branch points divided by the number of end points. The connectedness of the pigmented network will be higher for a globular pattern than a reticular pattern because globules do not connect. This variable (V27) will also be higher for a reticular pattern if the branches are broken.

The range of the average branch length in an incremental angular zone evaluated over all possible angles (V28) evaluates how the branch lengths change in different directions. If a reticular lesion has an irregular pigmented network where the branches in some regions are longer than in others, this variable (V28) will be high.

The range of the average branch brightness in an incremental angular zone evaluated over all possible angles (V29) quantifies the brightness of the branches in the same angular way that the previous variable (V28) quantifies branch lengths.

The range of the average number of branches in an incremental angular zone evaluated over all possible angles (V30) is another metric.

Figure 8:
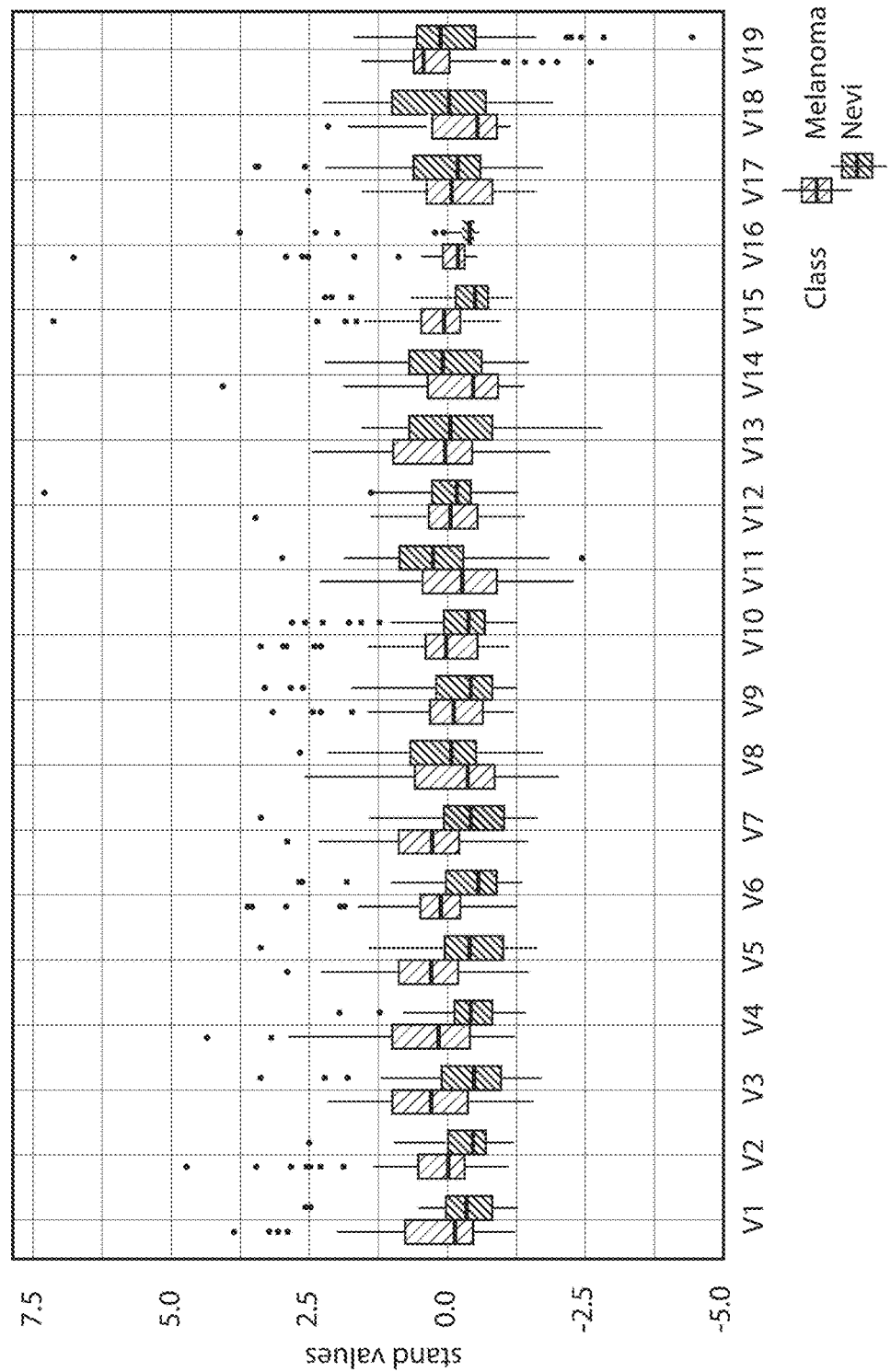
FIG. 8 is a visualization of the discriminative power of metrics used in the method of the invention.

FIG. 8 depicts the discriminative power of each of the metrics V1 through V19. Each box in the chart represents a range of values for a given metric according to whether the skin lesion in the sample is a melanoma or nevus (as determined by pathologist screening); therefore, each metric is associated with two columns of data points and two boxes. The vertical lines in each column represent barriers for atypical data and the points above and below represent potential outliers. Thus, the larger the vertical displacement of the boxes for nevus and melanoma, the more discriminating the metric. A shorter overall height of the boxes in the chart represents less uncertainly in the prediction for that metric.

Correlations of metrics to disease states may be obtained from a sample of lesions obtained from human subjects, containing known melanoma and nevi, and applying two-sided unpaired t-tests. Table 3 below tabulates P-values for preferred metrics in two-sided unpaired t-tests applied using the methods of the invention to a sample including melanoma and non-cancerous nevi (n=115 samples). In Table 3, a lower P-value represents a higher correlation of the metric with the correct prediction that a given lesion is melanoma. The discriminatory power of the metrics improves as the wavelength of illuminating light is shifted toward shorter wavelengths, particularly into the blue and ultraviolet. This is shown in Table 3, wherein metrics M1 through M16 correspond to (V1) through (V16) described above, and M17 through M27 correspond to (V20) through (V30) described above. Table 3 shows the P-values—the statistical correlation between a particular metric prediction and the occurrence of melanoma in a lesion—repeated for each wavelength of red, green and blue illuminating light. The P-values trend lower as the wavelength of illuminating light moves toward the blue.

TABLE 3

| Metric | Red Channel | Green Channel | Blue Channel |
|---|---|---|---|
| M1  | 0.038512853 | 0.005974978 | 0.005413393 |
| M2  | 0.064100668 | 0.004186356 | 0.000931948 |
| M3  | 0.051076855 | 0.049752151 | 0.004417105 |
| M4  | 0.015508981 | 0.004775704 | 0.000322272 |
| M5  | 0.053177386 | 0.000288015 | 3.11E−05 |
| M6  | 0.083413521 | 0.0017528   | 0.000203987 |
| M7  | 0.053177386 | 0.000288015 | 3.11E−05 |
| M8  | 0.06168296  | 0.355771648 | 0.373633602 |
| M9  | 0.18969333  | 0.941812711 | 0.51577414 |
| M10 | 0.764701562 | 0.118919328 | 0.071004505 |
| M11 | 0.223854987 | 0.017938675 | 0.001834162 |
| M12 | 0.595301519 | 0.341014351 | 0.566527499 |
| M13 | 0.000128953 | 0.014482528 | 0.023037402 |
| M14 | 0.019109506 | 0.050021307 | 0.041666677 |
| M15 | 0.013434262 | 0.005961503 | 0.000900939 |
| M16 | 0.042338391 | 0.068554129 | 0.046165566 |
| M17 | 1.67E−05    | 0.005296628 | 0.00494726 |
| M18 | 0.707233508 | 0.794075037 | 0.825754151 |
| M19 | 0.013854117 | 0.770162679 | 0.99699408 |
| M20 | 0.13132109  | 0.018472359 | 0.004819414 |
| M21 | 0.464474471 | 0.192611265 | 0.167729501 |
| M22 | 0.050291628 | 0.032035539 | 0.047297197 |
| M23 | 0.066784433 | 0.041333049 | 0.052544662 |
| M24 | 0.105241821 | 0.404152353 | 0.474939953 |
| M25 | 0.166005642 | 0.044997689 | 0.200169654 |

TABLE 3-continued

| Metric | Red Channel | Green Channel | Blue Channel |
|---|---|---|---|
| M26 | 0.021380908 | 0.339045255 | 0.857779693 |
| M27 | 7.43E−05    | 0.000717461 | 0.027130568 |

Figure 9:
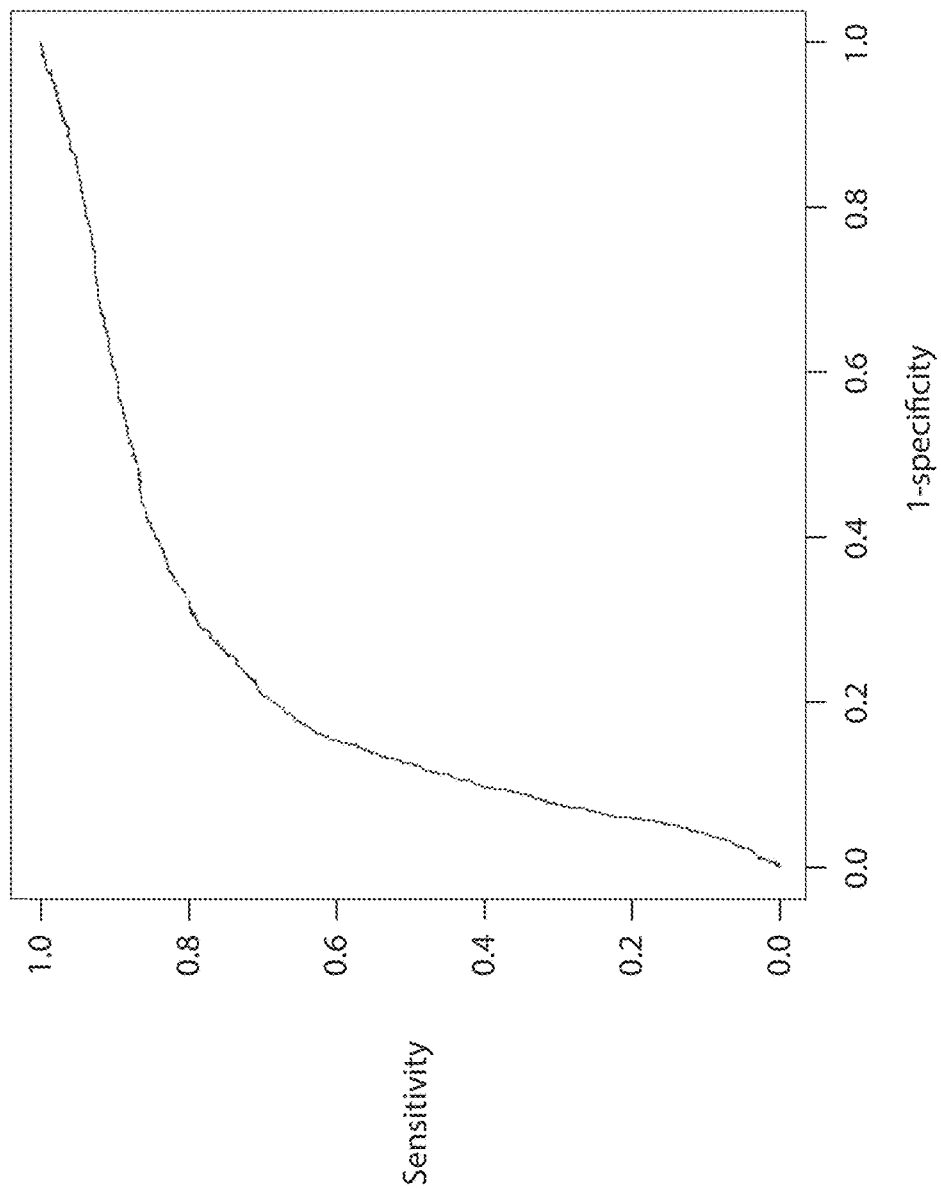
FIG. 9 is an example of a Receiver Operator Curve ("ROC curve") built using classifiers according to methods of the invention.

As used herein "classifiers" are combinations of metrics in functions built using multivariate methods to increase the predictive ability of the method to distinguish melanoma from nevi. Classifiers may be obtained and optimized according to known techniques by maximizing the performance of a set of classifiers in receiver operator curve ("ROC") maximization. An example of ROC maximization for classifiers distinguishing melanoma from nevi is reproduced in FIG. 9, which plots specificity (true negative rate) versus sensitivity (true positive rate), such that a maximum area under the curve in FIG. 9 represents an accurate classifier.

The output of a classifier is a percent likelihood that a lesion is melanoma, which may be coupled with a percent error or uncertainty for the classifier. This can be output for the user in any desired format. A dermatologist may want to see the underlying statistical information displayed as numbers and graphs, either on the device LCD screen, or on the screen of the computer communicating with the device. The ordinary patient may prefer an intuitive system of identifying potentially dangerous lesions, where the lesions most likely to be melanomas are identified with a red light and the least dangerous with a green light.

In order to develop the classifiers, a sample of nevi of known pathology was obtained and classifiers were developed using a "training" subset of the sample using both linear techniques (such as regressions and linear discriminant analysis) and nonlinear techniques (such as neural networks and decision tree algorithms) The following linear classifier is an example of a classifier developed from a training set having some predictive ability to discriminate between nevi and melanoma:

$$L = 0.16*\text{range} - 0.87*\text{edge} + 0.68$$

where range and edge are metrics defined above and L represents a classifier that may be compared to a threshold to yield a classification of melanoma or nevus. More robust classifiers can be created by incorporating more of the metrics, such as the classifier in the accompanying computer code that uses all the metrics. "Training" was possible because the pathology of the lesions was known from prior pathologist screening, and the metrics and constants may be selected to maximize the area under the ROC curve. Subsequently, the "trained" classifiers are applied to lesions having unknown pathology. (In the experimental setting this means that the investigator was blind to the pathology of the lesions and did not adjust the classifiers; in the real world setting the device will typically be applied only to lesions having unknown pathology, and the thresholds and classifiers will be pre-programmed) As would be apparent to one of ordinary skill in the art, a larger training sample and slight variation of the metrics will likely yield improved classifiers, without departing from the scope of the invention. Once obtained, the classifiers are applied to the image data of lesions whose pathology is unknown. According to the invention, a sensitivity/specificity of 86%/91% was obtained, with an overall diagnostic accuracy of 89%. This result is expected to improve with routine optimization at 99% sensitivity, the specificity was as high as 56% in some test sets, showing significant improvement over the prior art.

Using the camera in the embodiment of FIG. 1A and FIG. 1B for image data acquisition is straightforward, as described in the following sample operation protocol.

Routine Operation

1. Clean the imaging window at the distal imaging plane of the apparatus by wiping with an alcohol prep pad.
2. Identify and open the graphic user interface (operating software) on the desktop.
3. Enter the requested details about the patient and lesion.
4. Press play to activate a live imaging feed. Check to see that the LEDs have illuminated. The device should be emitting light.
5. Place a drop of water on the target skin lesion.
6. Press the imaging window against the skin centered on the lesion.
7. Verify on the touchscreen that the lesion is in the center of the image.
8. Verify that the contact is complete across the window without bubbles between the window and the subject's skin.
9. Touch "Acquire" on the touch screen and wait 3 seconds for acquisition.
10. Verify that the images were acquired by watching the playback that occurs after acquisition. In particular, check that:
    a. contact was maintained throughout the image acquisition (no bubbles)
    b. the device did not slip (i.e. the images did not shift laterally)
    c. the color image that displays at the end of playback is uniformly balanced. If contact and stability were insufficient, the color image will have sections that are unexpected, such as one half of the lesion appearing blue and the other half appearing red.
11. If contact and stability are not verified, re-stabilize and repeat acquisition.

The foregoing description of the preferred embodiments is for illustration and is not to be deemed as limiting the invention defined by the following claims. The primary application of the invention is to detect melanoma in humans and to distinguish cancerous from non-cancerous lesions. However, in principle, the apparatus and methods have broad application in the detection and display of other skin diseases and diseases in other human tissues. Moreover, using the clock sweep method of analyzing multispectral image data according to the invention lends itself to the development of improved metrics and more discriminating classifiers for the detection of melanoma, without departing from the scope of the invention. The foregoing descriptions of a clinical apparatus and cellular phone apparatus enable the person of ordinary skill to practice variants thereof without departing from the scope of the invention.

What is claimed is:

1. A method of diagnostically imaging at least one skin lesion on a subject's skin, comprising the steps of:
    illuminating with a first illumination system a first area on the subject's skin;
    obtaining wide field image data from the illuminated skin using a first camera having a first lens with a first wide field of view;
    processing the wide field image data to identify a target area within the first area on the subject's skin, the first area including a potential skin lesion;
    illuminating the target area with a second illumination system;
    obtaining second narrow field image data from the illuminated target area with a second camera having a second lens with a second narrow field of view narrower than the first wide field of view, the light of the second illumination system being set at one or more wavelengths, different from those of the first illumination system, for the second narrow field of view;
    processing the second narrow field image data to locate a center and border of the potential skin lesion and determine that the potential skin lesion is in fact in the target area;
    creating a line segment extending out from the center to the border;
    rotating the line segment about the center at a plurality of angles;
    sampling the brightness of the narrow field image data at a plurality of pixels along the line segment at said angles; and
    processing the brightness samples to obtain one or more metrics and/or classifiers for use in a diagnosis of the potential skin lesion.

2. The method according to claim 1, further comprising obtaining third narrow field image data from the target area with a third camera having a third narrow field of view narrower than the second narrow field of view, said third narrow field of view being the field of view of a confocal microscope.

3. The method according to claim 2, further comprising obtaining fourth narrow field image data from the target area with a fourth camera having a fourth narrow field of view narrower than the third field of view, said fourth narrow field of view being determined by Raman spectrometer.

4. The method according to claim 1, wherein processing the wide field image data includes statistical evaluation of the size and irregularity of lesions in the first area.

5. The method according to claim 1, wherein the one or more metrics and/or classifiers define the rotational distribution of one or more properties selected from the group consisting of [a] spatial texture features; [b] brightness features; [c] features of a lesion image edge/border, including the sharpness with which the lesion borders normal skin; [d] color variation of a lesion image; [e] variations in the features of the pigmented network including the length, shape, brightness and organization of pigmented network segments; and [f] oxygen saturation tissue as defined by an amount and ratio of oxyhemoglobin and deoxyhemoglobin said metrics and/or one or more classifiers being used to provide the diagnosis.

6. The method according to claim 1, wherein the wide field image data is red-green-blue image data.

7. The method according to claim 6, wherein the wide field image data is obtained with a camera integrated with a cellular phone.

8. The method according to claim 1, wherein the wide field image data is obtained with a camera worn on a user's body, capable of projecting images to the wearer, and having interactive processing capability.

9. The method according to claim 1, wherein the wide field image data is hyperspectral image data.

10. The method according to claim 1, wherein the second narrow field image data is red-green-blue image data.

11. The method according to claim 1, wherein the second narrow field image data is hyperspectral image data.

12. The method according to claim 1, wherein the first and second cameras, first and second lens, and first and second illumination systems are in a single camera unit, further comprising the step of respectively switching the first and second lenses and the first and second illumination systems to obtain the wide field image data and second narrow field image data.

13. The method according to claim 1, comprising successively processing meter scale image data, centimeter scale image data, millimeter scale image data and micrometer scale image data with respective scale focal length focusing systems to obtain diagnostic information at each respective focal length.

14. A system of diagnostic imaging of one or more skin lesions on a subject's skin, comprising:
   a wide field camera having a first lens with a wide field of view and a first illumination system adapted to illuminate a first area on the subject's skin corresponding to the first field of view;
   a narrow field camera having a second lens with a narrow field of view and a second illumination system at one or more wavelengths, different from those of the first illumination system, adapted to illuminate a target area of a potential skin lesion within the first area; and
   a processor operatively connected to the wide field camera and the narrow field camera adapted to obtain and process image data from the wide field camera and the narrow field camera, wherein the processor: (1) processes image data from the wide field camera to identify the target area, (2) processes the image data from the narrow field camera to locate a center and border of the potential skin lesion and determine that the potential skin lesion is in fact in the target area, (3) creates a line segment extending out from the center to the border, (4) rotates the line segment about the center at a plurality of angles, (5) samples the brightness of the image data from the narrow field camera at a plurality of pixels along the line segment at said angles, and (6) processes the brightness samples to provide one or more metrics and/or classifiers for use in a diagnosis of said potential skin lesion.

15. The system according to claim 14, wherein the first lens and second lens are incorporated in a single camera unit switchable from a wide field of view to a narrow field of view, the first lens having a longer focal length than the second lens.

16. The system according to claim 15, wherein the single camera unit further comprises the first illumination system and the second illumination system.

17. The system according to claim 15, wherein the first camera includes at least one Charged Coupled Device (CCD) sensor or Complementary Metal Oxide Semiconductor (CMOS) sensor detecting Red Green and Blue (RGB) light.

18. The system according to claim 15, wherein the first camera includes at least one Charged Coupled Device (CCD) sensor or Complementary Metal Oxide Semiconductor (CMOS) sensor detecting hyperspectral wavelengths of light.

19. The system according to claim 14, wherein the processor the one or more metrics and/or classifiers define the rotational distribution of properties selected from the group consisting of [a] spatial texture features; [b] brightness features or [c] features of the lesion image edge/border, including the sharpness with which the lesion borders normal skin; [d] color variation of a lesion on the subject's skin; [e] variations in features of a pigmented network including the length, shape, brightness and organization of pigmented network segments; and [f] oxygen saturation of tissue as defined by the amount and ratio of oxyhemoglobin and deoxyhemoglobin said metrics and/or one or more classifiers being used to provide the diagnosis.

20. The system according to claim 14, wherein one of the first illumination system and the second illumination system provides illumination at RGB wavelengths of light, and the other illumination system provides illumination at hyperspectral wavelengths of light.

* * * * *